(12) United States Patent
Kozikowski et al.

(10) Patent No.: US 8,153,657 B2
(45) Date of Patent: Apr. 10, 2012

(54) DOPAMINE-, NOREPINEPHRINE- AND SEROTONIN-TRANSPORTER-SELECTIVE HETEROCYCLIC COMPOUNDS AND THEIR THERAPEUTIC APPLICATIONS

(75) Inventors: Alan P. Kozikowski, Chicago, IL (US); Jia Zhou, Washington, DC (US)

(73) Assignee: Georgetown University, Washington, DC (US)

( * ) Notice: Subject to any disclaimer, the term of this patent is extended or adjusted under 35 U.S.C. 154(b) by 1318 days.

(21) Appl. No.: 10/576,620

(22) PCT Filed: Oct. 22, 2004

(86) PCT No.: PCT/US2004/035162
§ 371 (c)(1),
(2), (4) Date: Mar. 8, 2007

(87) PCT Pub. No.: WO2005/041875
PCT Pub. Date: May 12, 2005

(65) Prior Publication Data
US 2007/0254918 A1 Nov. 1, 2007

Related U.S. Application Data

(60) Provisional application No. 60/513,521, filed on Oct. 22, 2003.

(51) Int. Cl.
*A61K 31/445* (2006.01)
*C07D 211/54* (2006.01)

(52) U.S. Cl. ........ 514/316; 514/317; 514/321; 514/323; 514/326; 514/330; 514/331; 546/187; 546/197; 546/201; 546/207; 546/225; 546/229; 546/236; 546/237; 546/238; 546/240; 546/248

(58) Field of Classification Search .................. 514/315, 514/317, 321, 323, 326, 327, 330, 331; 546/197, 546/201, 207, 216, 225, 229, 236, 237, 238, 546/240, 248
See application file for complete search history.

(56) References Cited

U.S. PATENT DOCUMENTS

| 4,877,799 | A | 10/1989 | Drejer et al. |
| 6,127,366 | A | 10/2000 | Kim et al. |
| 6,448,243 | B1 | 9/2002 | Kitazawa et al. |
| 7,517,892 | B2 * | 4/2009 | Aquila et al. ............ 514/317 |

FOREIGN PATENT DOCUMENTS

| WO | WO-00/20390 A1 | 4/2000 |
| WO | WO-01/04093 A2 | 1/2001 |

OTHER PUBLICATIONS

Jones et al. "preparation of 4-(4- . . . " CA 134:100766 (2001).*
International Search Report for PCT/US04/35162, Sep. 22, 2009.

* cited by examiner

*Primary Examiner* — Celia Chang
(74) *Attorney, Agent, or Firm* — Foley Hoag LLP

(57) ABSTRACT

One aspect of the invention relates to piperidine compounds that are useful as inhibitors of monoamine transporters. The invention also relates to pharmaceutical compositions, comprising a piperidine compound of the invention. Another aspect of the present invention relates to the use of the aforementioned compounds in a method of treating a disorder of the central nervous system in a mammal.

40 Claims, 10 Drawing Sheets

Inhibition of Reuptake at Monoamine Transporters ($K_i \pm$ SEM (nM))

| Compound | ClogP 'Daytime' | ClogP 'KowWin' | [³H]DA Uptake | [³H]5-HT Uptake | [³H]-NE Uptake |
|---|---|---|---|---|---|
| Cocaine | | | 259 ± 19.9 | 155 ± 0.40 | 108 ± 3.50 |
| Fluoxetine | | | 4,580 ± 550 | 7.34 ± 0.66 | 167.4 ± 14.86 |
| CTDP 31,181 | | | 44.5±8.5 | 743.5±2.5 | 102.0±14.0 |
|  JZ-III-46 | 4.41 | 4.85 | 375.7±54.0 | 238.0±48.8 | 423.6±53.4 |
|  JZ-III-48 | 3.15 | 3.72 | 80.4±23.3 | 208.3±46.5 | 25.0±6.2 |
|  JZ-III-52 | 2.19 | 2.84 | 58.9±18.6 | 556.9±150.1 | 38.6±4.9 |

| Compound | ClogP 'Daytime' | ClogP 'KowWin' | [³H]DA Uptake | [³H]5-HT Uptake | [³H]-NE Uptake |
|---|---|---|---|---|---|
|  JZ-III-54-1 | 1.30 | | 164.0±37.7 | 2,649±767 | 14.8±6.1 |
|  JZ-III-57 | 1.46 | 1.05 | 209.3±25.1 | 5,790±1712 | 177.5±48.5 |
|  JZ-III-59 | 1.64 | 2.58 | 231.0±93.2 | 808.5±36.0 | 53.0±16.3 |
|  JZ-III-62 | 1.87 | 2.71 | 85.4±19.3 | 226.9±6.7 | 15.1±2.0 |

| COMPOUND | ClogP 'Daytime' | ClogP 'KowWin' | [³H]DA Uptake | [³H]5-HT Uptake | [³H]-NE Uptake |
|---|---|---|---|---|---|
|  JZ-III-85 | 1.14 | 0.92 | 55.2±7.6 | 1,795±67 | 11.6±1.2 |
|  JZ-III-82 | 0.73 | 0.24 | 121.2±31.6 | 269.9±9.7 | 70.2±7.2 |
|  JZ-III-84 | 2.81 | 3.21 | 16.1±4.5 | 158.0±4.6 | 0.94±0.27 |
|  JZ-III-86 | 3.71 | 4.21 | 35.1±10.8 | 57.1±17.9 | 3.6±1.5 |

| Compound | ClogP 'Daytime' | ClogP 'KowWin' | [³H]DA Uptake | [³H]5-HT Uptake | [³H]-NE Uptake |
|---|---|---|---|---|---|
|  JZ-III-87 | 5.46 | 5.67 | 68.3±21.9 | 6.7±1.5 | 4.5±1.2 |
|  JZ-III-90 | 4.55 | 3.53 | 31.6±12.1 | 199.3±14.4 | 17.9±5.8 |
|  JZ-III-91 | 2.85 | 2.07 | 9.1±2.9 | 87.1±17.0 | 29.2±3.8 |
|  JZ-IV-5 | 2.29 | 3.30 | 13.0±2.6 | 109.9±44.9 | 25.2±2.3 |

| COMPOUND | ClogP 'Daytime' | ClogP 'KowWin' | [³H]DA Uptake | [³H]5-HT Uptake | [³H]-NE Uptake |
|---|---|---|---|---|---|
|  JZ-IV-7 | 3.80 | 4.88 | 83.3±1.2 | 4.5±0.8 | 0.68±0.25 |
|  JZ-IV-10 | 3.13 | 4.21 | 1.01±0.22 | 1.12±0.42 | 0.81±0.12 |
|  JZ-IV-14 | 0.78 | 1.51 | 164.4±27.5 | 2,033±573 | 86.2±2.3 |
|  JZ-IV-15 | 1.62 | 2.42 | 247.7±77.5 | 472.6±60.0 | 20.2±2.8 |

| Compound | ClogP 'Daytime' | ClogP 'KowWin' | [³H]DA Uptake | [³H]5-HT Uptake | [³H]-NE Uptake |
|---|---|---|---|---|---|
|  JZ-IV-16 | 3.08 | 3.08 | 378.6±89.7 | 824.6±99.1 | 459.8±11.2 |
|  JZ-IV-17 | 3.31 | 4.17 | 125.7±14.7 | 220.9±45.6 | 31.5±9.7 |
|  JZ-IV-21 | 1.56 | 2.03 | 1,653±56 | 1,079±269 | 217.6±13.9 |
|  JZ-IV-22 | 2.87 | 3.51 | 51.0±16.4 | 13.3±2.9 | 0.56±0.09 |

Figure 7

| Compound | ClogP 'Daytime' | ClogP 'KowWin' | [$^3$H]DA Uptake | [$^3$H]5-HT Uptake | [$^3$H]-NE Uptake |
|---|---|---|---|---|---|
| JZ-IV-23 | 2.89 | 3.52 | 116.1±46.1 | 88.3±21.7 | 27.2±7.4 |
| JZ-IV-25 | 1.75 | 2.63 | 113.6±32.1 | 170.0±5.8 | 10.0±0.07 |
| JZ-IV-27 | 2.16 | 1.72 | 2,884±654 | 923.8±138.5 | 1,249±19 |
| JZ-IV-34 | 1.95 | 1.07 | 11.8±1.1 | 2,183±373 | 42.0±16.0 |

| Compound | ClogP 'Daytime' | ClogP 'KowWin' | [³H]DA Uptake | [³H]5-HT Uptake | [³H]-NE Uptake |
|---|---|---|---|---|---|
|  JZ-IV-35 | 3.41 | 3.91 | 50.2±15.3 | 190.6±56.8 | 6.1±1.8 |
|  JZ-IV-36 | 1.76 | 1.77 | 14.7±4.6 | 469.1±36.2 | 24.7±5.7 |
|  JZ-IV-37 | 0.24 | 0.84 | 107.8±29.1 | 774.9±95.9 | 31.1±3.4 |

Figure 9

Inhibition of Reuptake at Monoamine Transporters ($K_i \pm$ SEM (nM))

| Compound | 5-HT/DA | NE/DA | NE/5-HT |
|---|---|---|---|
| Cocaine | 0.37 | 0.20 | 0.70 |
| Fluoxetine | 0.002 | 0.04 | 22.8 |
| CTDP 31,181 | 16.71 | 2.29 | 0.14 |
| JZ-III-46 | 0.63 | 1.13 | 1.77 |
| JZ-III-48 | 2.59 | 0.31 | 0.12 |
| JZ-III-52 | 3.50 | 0.24 | 0.07 |
| JZ-III-54-1 | 16.2 | 0.09 | 0.005 |
| JZ-III-57 | 27.6 | 0.85 | 0.03 |
| JZ-III-59 | 3.5 | 0.23 | 0.07 |
| JZ-III-62 | 2.66 | 0.18 | 0.07 |
| JZ-III-85 | 32.5 | 0.21 | 0.001 |
| JZ-III-82 | 2.23 | 0.58 | 0.26 |
| JZ-III-84 | 9.81 | 0.06 | 0.005 |
| JZ-III-86 | 1.63 | 0.10 | 0.06 |
| JZ-III-87 | 0.10 | 0.07 | 0.67 |
| JZ-III-90 | 6.31 | 0.57 | 0.09 |
| JZ-III-91 | 9.57 | 3.21 | 0.34 |

Figure 10

| Compound | 5-HT/DA | NE/DA | NE/5-HT |
|---|---|---|---|
| JZ-IV-5 | 8.45 | 1.94 | 0.23 |
| JZ-IV-7 | 0.05 | 0.001 | 0.15 |
| JZ-IV-10 | 1.11 | 0.80 | 0.72 |
| JZ-IV-14 | 12.37 | 0.52 | 0.04 |
| JZ-IV-15 | 1.91 | 0.08 | 0.04 |
| JZ-IV-16 | 2.18 | 1.21 | 0.56 |
| JZ-IV-17 | 1.76 | 0.25 | 0.14 |
| JZ-IV-21 | 0.65 | 0.13 | 0.20 |
| JZ-IV-22 | 0.26 | 0.01 | 0.04 |
| JZ-IV-23 | 0.76 | 0.23 | 0.31 |
| JZ-IV-25 | 1.50 | 0.08 | 0.06 |
| JZ-IV-27 | 0.32 | 0.43 | 1.35 |
| JZ-IV-34 | 185 | 3.56 | 0.02 |
| JZ-IV-35 | 3.80 | 0.12 | 0.03 |
| JZ-IV-36 | 31.9 | 1.68 | 0.05 |
| JZ-IV-37 | 7.19 | 0.29 | 0.04 |

DOPAMINE-, NOREPINEPHRINE- AND SEROTONIN-TRANSPORTER-SELECTIVE HETEROCYCLIC COMPOUNDS AND THEIR THERAPEUTIC APPLICATIONS

RELATED APPLICATIONS

This application claims the benefit of priority to Patent Cooperation Treaty Application number PCT/US2004/035162, filed Oct. 22, 2004; which claims the benefit of the filing date of U.S. Provisional Patent Application Ser. No. 60/513,521, filed Oct. 22, 2003.

GOVERNMENT SUPPORT

This invention was made with support provided by the National Institutes of Health and National Institute of Drug Abuse (Grant Nos. DA10458 and DA11548); therefore, the government has certain rights to the invention.

BACKGROUND OF THE INVENTION

Psychiatric and neurological disorders are known to afflict millions of people worldwide resulting in substantial undue suffering. One serious and often destructive psychiatric disorder is depression. This disease is one of the most common and destructive illnesses prevalent in the United States and is estimated to afflict 35-40 million Americans at some point during their lives. Other important psychiatric and neurological disorders are anxiety disorders, mood disorders, personality disorders, psychosexual disorders, schizophrenia, drug abuse and dependence, and eating disorders. These disorders are known to affect people of all ages and the disorder may persist for a duration of a few weeks up to several decades.

Advances in neuroscience and molecular biology have lead to a better understanding of the roles of various biochemicals that cause psychiatric and neurological disorders. Research efforts have revealed that dopamine, norepinephrine, and serotonin play a role in many of these disorders. These biochemicals are important neurotransmitters that are implicated in a wide array of critical physiological processes.

Dopamine affects brain processes that control movement, emotional response, and ability to experience pleasure and pain. Regulation of dopamine plays a crucial role in our mental and physical health. It is thought that the dopamine transporter (DAT) is a primary mechanism for terminating the effects of synaptic dopamine and maintaining homeostatic levels of extracellular dopamine in the brain. Giros et al. *Nature* 1996, 379, 696. The dopamine transporter has been an important target for several drugs including methylphenidate, pemoline, and bupropion.

Norepinephrine (NE), also called noradrenaline, is a neurotransmitter that doubles part-time as a hormone. As a neurotransmitter, norepinephrine helps to regulate arousal dreaming, and moods. As a hormone, it acts to increase blood pressure, constrict blood vessels and increase heart rate, all of which are responses to stress.

Serotonin (5-hydroxytryptamine, 5-HT) is widely distributed in animals and plants. In the human body, serotonin is found mainly in the intestinal wall (where it causes increased gastrointestinal motility), blood vessels (where large vessels are constricted), and the central nervous system (CNS). Serotonin may be obtained from a variety of dietary sources; however, endogenous serotonin is synthesized in situ from tryptophan through the actions of the enzymes tryptophan hydroxylase and aromatic L-amino acid decarboxylase. The functions of serotonin are numerous and include control of appetite, sleep, memory and learning, temperature regulation, mood, behavior (including sexual and hallucinogenic behavior), cardiovascular function, muscle contraction, endocrine regulation, and depression.

The ability to treat psychiatric and neurological disorders has increased significantly over the last several decades. It has been found that compounds that selectively modulate the activity of dopamine, norepinephrine, or serotonin are effective treatments. For example, most forms of depression are associated with a deficiency of norepinephrine and/or serotonin at functionally important adrenergic or serotonergic receptors. Thus, treatment approaches have involved the use of agents (stimulants) that mimic norepinephrine, pharmaceuticals (MAOIs) that increase the levels of NE and 5-HT by inhibiting their metabolism, and drugs that increase these levels at the receptor by inhibiting the uptake of NE and 5-HT.

One class of antidepressants are tricyclic antidepressants (TCAs) which function by blocking the uptake of norepinephrine and, to varying degrees, the uptake of 5-HT. Within the class of TCA's, tertiary amines such as imipramine and amitriptyline are more selective inhibitors of 5-HT than catecholamines, compared with secondary amines such as desipramine. Trazodone and fluoxetine, both of which are marketed in the United States, serve to regulate the level of serotonine. Trazodone mediates the actions of 5-HT while fluoxetin is a selective inhibitor of 5-HT reuptake.

Narcolepsy is a disease that is thought to be caused by abnormalities in brain chemistry. Narcolepsy is a potentially disabling, lifelong condition estimated to afflict about one in every 1,000 people in the United States. The two primary symptoms of narcolepsy are excessive daytime sleepiness and cataplexy. People with narcolepsy are unable to resist falling asleep and do so regardless of the number of hours slept the previous night. Frequently, people with narcolepsy fall asleep at inappropriate times, for example while eating or in the middle of a conversation. Currently, there is no known cure for narcolepsy; however, the severity of the symptoms can be minimized with varying degrees of success with medications and adjustments of lifestyle.

The effects of excessive daytime sleepiness can be reduced by administration of provigil. Provigil is a wake-promoting agent allowing people with narcolepsy to participate in daily activities. However, provigil has been linked to side effects in some patients. These side effects include nausea, infection, nervousness, anxiety and/or insomnia.

Despite recent advances in the treatment of psychiatric and neurological disorders, many patients do not have satisfactory treatment options because they do not respond to a drug or the drug has intolerable side effects. For example, it is estimated that up to 30% of clinically diagnosed cases of depression are resistant to all known forms of drug therapy. In addition, many of the antidepressant drugs are linked to anticholinergic actions, cardiotoxicity, sedation, and/or weight gain. Hence, the need exists for new drugs to treat these patients, in addition to drugs with fewer side effects.

SUMMARY OF THE INVENTION

The invention generally relates to piperidine compounds that are useful as inhibitors of monoamine transporters. In a preferred embodiment, the compounds of the invention comprise a piperidine ring wherein the nitrogen atom of the piperidine is substituted with a methyl group. In certain embodiments, the nitrogen atom of the piperidine ring may be oxidized to the corresponding N-oxide. In certain embodiments, the piperidine ring is substituted at the 4-position with an optionally substituted phenyl group. In a preferred embodiment, the piperidine ring is substituted at the 4-position with a 3-chlorophenyl group. The piperidine compounds of the invention are also substituted at the 3-position with an optionally substituted alkyl thioether, sulfoxide, or sulfone group. In a preferred embodiment, the substituent at the 3-position of the piperidine ring comprises a thioether group. The invention also relates to pharmaceutical compositions, comprising a piperidine compound of the invention.

Another aspect of the present invention relates to the use of the aforementioned compounds in a method of treating a disorder of the central nervous system in a mammal. In certain embodiments, said mammalian central-nervous-system disorder is selected from the group consisting of depression, anxiety disorders, mood disorders, personality disorders, psychosexual disorders, schizophrenia, eating disorders, drug dependence, drug abuse, drug addiction, ADHD, premenstrual dysphoria, Parkinson's disease, Alzheimer's disease, bipolar disorder, chronic pain, migraine, epilepsy, multiple sclerosis, stroke, trauma, mania, obsessive-compulsive disorder, obesity, cocaine addiction and narcolepsy.

BRIEF DESCRIPTION OF THE FIGURES

FIG. 7 depicts tabulated data for the inhibition of reuptake at monoamine transporters for various compounds.

FIG. 9 depicts tabulated data for the inhibition of reuptake at monoamine transporters for various compounds.

FIG. 10 depicts tabulated data for the inhibition of reuptake at monoamine transporters for various compounds.

DETAILED DESCRIPTION OF THE INVENTION

Figure 1:
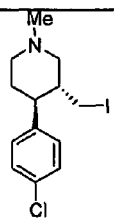
FIG. 1 depicts tabulated data for the inhibition of reuptake at monoamine transporters for various compounds.
Figure 1:
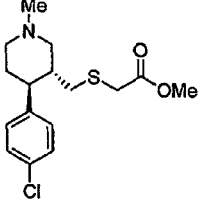
Figure 1:
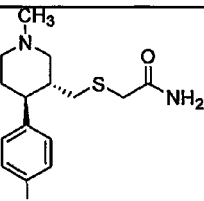

The invention relates generally to piperidine-containing compounds that are useful for the treatment of various psychiatric and neurological disorders. The compounds of the invention have been shown to inhibit momoamine transporters. Thus, the compounds of the invention may be used to treat sleep problems, depression, and drug abuse in addition to other psychiatric disorders. The compounds may also be used to treat a disorder of the central nervous system in a mammal. In certain embodiments, said mammalian central-nervous-system disorder is selected from the group consisting of depression, anxiety disorders, mood disorders, personality disorders, psychosexual disorders, schizophrenia, eating disorders, drug dependence, drug abuse, drug addiction, ADHD, premenstrual dysphoria, Parkinson's disease, Alzheimer's disease, bipolar disorder, chronic pain, migraine, epilepsy, multiple sclerosis, stroke, trauma, mania, obsessive-compulsive disorder, obesity, cocaine addiction and narcolepsy.

In certain embodiments, the compounds of the present invention have a piperidine core substituted at three positions. In preferred embodiments, the nitrogen atom of the piperidine ring is substituted with an alkyl group. In a more preferred embodiment, the nitrogen atom of the piperidine ring is substituted with a methyl group. In certain embodiments, the nitrogen atom of the piperidine ring may be oxidized to the corresponding N-oxide. The piperidine ring may be substituted at the 4-position. In certain embodiments, the piperidine ring is substituted at the 4-position with an optionally substituted phenyl group. In a preferred embodiment, the piperidine ring is substituted at the 4-position with a 3-chlorophenyl group. The piperidine compounds of the invention are substituted at the 3-position with an optionally substituted alkyl thioether, sulfoxide, or sulfone group. In a preferred embodiment, the substituent at the 3-position of the piperidine ring comprises a thioether group.

The present invention also relates to pharmaceutical compositions comprising the piperidine compounds of the invention. In certain embodiments, the pharmaceutical composition comprises a pharmaceutically acceptable salt of the piperidine compounds.

The piperidine compounds of the invention have been tested for their ability to inhibit the uptake of dopamine, serotonin, and norepinephrine. The studies indicate that in certain cases it is preferable to have a thioether group in the substituent located at the 3-position of the piperidine ring. The inhibition studies also revealed that in certain cases it is advantageous to have an amide group attached to the terminus of the substituent that is attached to the 3-position of the piperidine ring.

The present invention also relates to a method of modulating the activity of a dopamine, serotonin, or norepinephrine receptor or transporter comprising the step of administering a therapeutically effective amount of the compounds of the invention. In certain embodiments, the invention relates to a method of treating addiction, anxiety, or depression.

DEFINITIONS

For convenience, certain terms employed in the specification, examples, and appended claims are collected here.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure. Representative alkyl groups include: methyl, ethyl, propyl, isopropyl, butyl, sec-butyl, isobutyl, pentyl, hexyl, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles," "heteroaromatics," or "heteroaryl." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

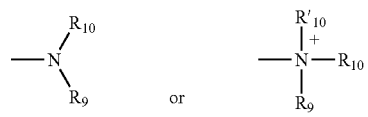

wherein $R_9$, $R_{10}$ and $R'_{10}$ each independently represent a group permitted by the rules of valence.

The term "acylamino" is art-recognized and refers to a moiety that can be represented by the general formula:

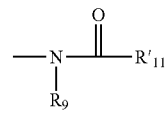

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

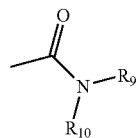

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

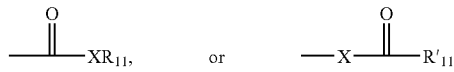

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R'_{11}$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

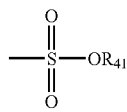

in which $R_{41}$ is an electron pair, hydrogen, alkyl, cycloalkyl, or aryl.

The term "oxadiazole" is art recognized and refers to a five-member ring comprising two nitrogen atoms, one oxygen atom, and two carbon atoms. A representative example of an oxadiazole is 3-methyl-1,2,4-oxadiazol-5-yl represented by the general formula:

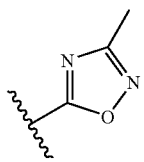

The terms triflyl tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

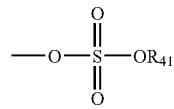

in which $R_{41}$ is as defined above.

The term "sulfonylamino" is art recognized and includes a moiety that can be represented by the general formula:

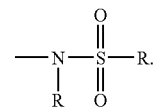

The term "sulfamoyl" is art-recognized and includes a moiety that can be represented by the general formula:

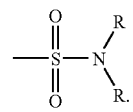

The term "sulfonyl", as used herein, refers to a moiety that can be represented by the general formula:

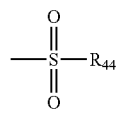

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

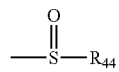

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

Sleep-Wake Regulation

The monoamines serotonin (5-HT), norepinephrine (NE) and histamine (HA), neuropeptides, including hypocretin (orexin), and other transmitters, including acetylcholine, GABA, and adenosine have been prominently implicated in sleep-wake regulation. In contrast, many authors have assigned only a marginal role for dopamine (DA) in sleep-wake control. See Steinfels et al. *Brain Research* 1983, 258, 217. Electrical activities of acetylcholine, NE, 5-HT, and HA (See Steininger et al. *Brain Research* 1999, 840, 138) neurons display robust changes across sleep-wake states that contrast with the limited alterations in firing rates of DA neurons across stages of sleep and wakefulness. The latter forms the basis of contemporary belief that alteration in acetylcholine, 5-HT, NE, or HA are more critically involved in regulating the cortical electroencephalogram (EEG) desynchronization characteristics of wakefulness, whereas dopaminergic activity is thought to mediate motor-related aspects of behaviors. See Steinfels et al., *Brain Research* 1983, 258, 217.

The lack of covariance between electrophysiological measures and sleep stages does not, however, obviate a role for dopamine in arousal state control. Indeed, the terminal release of dopamine varies in concert with arousal states. See Trulson, M. *Brain Res. Bull.* 1985, 15, 221. In addition, lesions of dopaminergic cell groups in the ventral tegmentum that project to the forebrain produce marked reduction in behavioral arousal, and human Parkinson's disease patients, who exhibit consistent dopaminergic lesions but inconsistent alterations in other monoamines, experience severe sleep disorders. See Aldrich M, In: Principles and practice of sleep medicine (Kryger M H, Roth T, Dement W E, eds), pp 1051. Philadelphia: Saunders, 2000.

Uncertainties have also persisted about the molecular bases of efficacious wake-promoting compounds, such as amphetamines and modafinil. Amphetamines block plasma membrane transporters for DA, NE, and 5-HT and inhibit the vesicular monoamine transporter (VMAT2), releasing monoamines from the synaptic vesicles into which VMAT2 pumps them. Noradrenergic mechanisms have been proposed to explain the wake-promoting effects of amphetamine-like stimulants. However, dopamine-specific reuptake blockers can promote wakefulness in normal and sleep-disordered narcoleptic animals better than NE transporter-selective blockers. Furthermore, the wake-promoting effect of amphetamine is maintained after severe reduction of brain norepinephrine produced by lesions of the noradrenergic cells of the locus ceruleus in cats.

The mode of action of modafinil, a wake-promoting compound used in the treatment of sleepiness associated with narcolepsy (US Modafinil in Narcolepsy Multicenter Study Group, 1998), is even more uncertain. Studies have suggested that modafinil increases wakefulness by activating $\alpha$-1 noradrenergic transmission or hypothalamic cells that contain the peptide hypocretin (See Chemelli et al. *Cell* 1999, 98, 437), or that it may work by modulating GABAergic tone (See Ferraro et al. *Eur. J. Pharmacol.* 1996, 306, 33). To identify the molecular basis for the wake-promoting effects of amphetamines and modafinil, Wisor and coworkers studied the responses to these compounds in narcoleptic canines, a genetic model for excessive sleepiness, and in dopamine transporter (DAT) knock-out mice. See Wisor, J. P.; Nishino, S.; Sora, I.; Uhl, G. H.; Mignot, E.; Edgar, D. M. *J. of Neuroscience* 2001, 21, 1787.

In the study by Wisor and coworkers, polygraphic recordings and caudate microdialysate dopamine measurements in narcoleptic dogs revealed that the wake-promoting antinarcoleptic compounds modafinil and amphetamine increase extracellular dopamine in a hypocretin receptor 2-independent manner. In mice, deletion of the dopamine transporter (DAT) gene reduced non-rapid eye movement sleep time and increased wakefulness consolidation independently from locomotor effects. DAT knock-out mice were also unresponsive to the normally robust wake-promoting action of modafinil, methamphetamine, and the selective DAT blocker GBR12909 but were hypersensitive to the wake-promoting effects of caffeine. Thus, dopamine transporters play an important role in sleep regulation and are necessary for the specific wake-promoting action of amphetamines and modafinil.

The finding that a DAT gene deletion alters baseline sleep and responsiveness to the major therapeutic wake-promoting agents has important clinical applications. Severe and often untreated sleep disorders are common in patients with dopaminergic dysfunction caused by Parkinson's disease and Huntington's chorea. Dopamine metabolism and receptor abnormalities also occur in disorders of excessive daytime sleepiness, such as narcolepsy, and in normal aging. The current data, combined with observations that specific DAT gene polymorphic markers (See Gill et al. *Mol. Psychiatry.* 1997, 2, 311) and sleep disorders are associated with attention deficit hyperactivity disorder, suggest that human variants at the DAT gene locus could predispose to vulnerability to sleep-wake disorders. Finally, the observations with DAT knock-outs provide a new major target for development of more efficacious wake-promoting drugs. The clinical safety profile, low abuse potential, and clinical success of modafinil suggest that selective DAT inhibitors can have useful clinical applications and low side effect profiles when compared with classical amphetamine-like stimulants. Because amphetamine-like compounds are now prescribed to millions of patients with a wide variety of sleep and psychiatric disorders, the utility of highly selective DAT inhibitors may deserve reconsideration.

Narcolepsy is a sleep disorder characterized by excessive daytime sleepiness (EDS) and dissociated manifestations of REM sleep, namely cataplexy (sudden onset of muscle atonia induced by emotional excitation), hypnagogic hallucinations, and sleep paralysis. Central nervous system (CNS) stimulants, amphetamines and amphetamine-like compounds (methylphenidate and pemoline), are the most commonly used pharmacological treatments for EDS in narcolepsy. Amphetamine-like stimulants at doses effective to treat EDS, however, have little beneficial effects on REM sleep-related symptoms, and antidepressants or monoamine oxidase inhibitors are thus also required to treat these symptoms. The success of these pharmacological approaches, however, is limited by the occurrence of multiple side effects and the development of drug tolerance.

Amphetamine-like stimulants are the most potent and efficacious wake-promoting compounds currently available, but little is known regarding their mode of action on sleep and wakefulness. These agents have multiple pharmacological properties, such as increasing monoamine release, blocking monoamine reuptake and inhibiting monoamine oxidase (see Parkes J D. Daytime Drowsiness. In: Parkes J D. Sleep and Its Disorders. London: W B Saunders, 1985b, pp. 267 for review). These properties contribute to the global enhancement of central monoaminergic transmission and are not selective for any single monoamine (DA, NE, or serotonin [5-HT]). The specific pharmacological property by which these compounds enhance wakefulness is still being debated and either or both increased NE or DA transmission have been suggested to be involved. For many years, pharmacologists have studied the effects of these compounds on locomotor activity or on barbiturate-induced locomotor depression in rodents and used these effects as an index of their "alerting" effects. Amphetamine-like stimulants, DA uptake inhibitors, and DA agonists at high doses, have similar CNS stimulant effects, suggesting dopaminergic mediation of wake promotion. Other investigators have also suggested adrenergic mediation of CNS stimulants for locomotor activation (See Taylor, J. R.; Robbins, T. W. *Psychopharmacology* 1984, 84, 405), but this effect may not directly represent the wake-promoting effects of these compounds. Furthermore, much higher doses of CNS stimulants are generally required to increase locomotor activity versus those to induce wakefulness in vivo. In addition, some wake-inducing compounds such as modafinil promote wakefulness, as evidenced by polygraphic recordings, without significantly increasing locomotor activity. See Shelton et al. *Sleep* 1995, 18, 817. Additional studies using selective DA and NE compounds and EEG recordings are thus needed to address these controversies.

As noted above, amphetamine-like stimulants are commonly used to treat sleepiness in narcolepsy. These compounds have little effect on rapid eye movement (REM) sleep-related symptoms, such as cataplexy, and antidepressants (monoamine uptake inhibitors) are usually required to treat these symptoms. Although amphetamine-like stimulants and antidepressants enhance monoaminergic transmission, these compounds are non-selective for each monoamine, and the exact mechanisms mediating how these compounds induce wakefulness and modulate REM sleep are not known. In order to evaluate the relative importance of dopaminergic and noradrenergic transmission in the mediation of these effects, Nishino and coworkers tested five dopamine (DA) uptake inhibitors (mazindol, GBR-12909, bupropion, nomifensine and aminepine), two norepinephrine (NE) uptake inhibitors (nisoxetine and desipramine), d-amphetamine, and modafinil, a non-amphetamine stimulant, in control and narcoleptic canines. See Nishino, S.; Mao, J.; Sampathkumaran, R.; Shelton, J.; Mignot, E. *Sleep Research Online* 1998, 1, 49. All stimulants and dopaminergic uptake inhibitors were found to dose-dependently increase wakefulness in control and narcoleptic animals. The in vivo potencies of DA uptake inhibitors and modafinil on wake significantly correlated with their in vitro affinities to the DA and not the NE transporter. DA uptake inhibitors also moderately reduced REM sleep, but this effect was most likely secondary to slow wave sleep (SWS) suppression, since selective DA uptake inhibitors reduced both REM sleep and SWS proportionally. In contrast, selective NE uptake inhibitors had little effect on wakefulness, but potently reduced REM sleep. These results suggest that presynaptic activation of DA transmission is critical for the pharmacological control of wakefulness, while that of the NE system is critical for REM sleep regulation. These results also suggest that presynaptic activation of DA transmission is a key pharmacological property mediating the wake-promoting effects of currently available CNS stimulants.

The results of the study by Nishino and coworkers demonstrate that increased DA transmission using uptake inhibitors or release enhancers preferentially modulates EEG arousal in normal and pathological conditions. In contrast, presynaptic modulation of NE systems has preferential effects on REM sleep and REM sleep-related phenomena. The two axial symptoms of narcolepsy, EDS and cataplexy, are thus pharmacologically regulated differently, and dysfunctions of both the dopaminergic and the noradrenergic systems may be involved in the pathophysiology of narcolepsy. This interpretation further explains why two different types of drugs, namely amphetamine-like stimulants and tricyclic antidepressants must be used for the treatment of EDS and REM sleep-related symptoms, respectively, in most human narcoleptic subjects.

Compounds of the Invention

One aspect of the present invention relates to a compound represented by formula I:

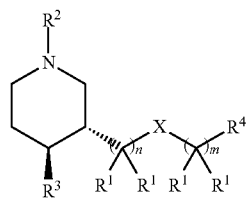

wherein
$R^1$ represents independently for each occurrence H or alkyl;
$R^2$ is H, alkyl, aryl, aralkyl, or —C(O)$R^5$;
$R^3$ is aryl, heteroaryl, or aralkyl;
$R^4$ is hydrogen, hydroxyl, aryl, heteroaryl, O$R^5$, CO$_2$$R^6$, C(O)N($R^6$)$_2$, C(O)NHOH, OC(O)$R^5$, or oxadiazole;
$R^5$ is alkyl, aryl, heteroaryl, or aralkyl;
$R^6$ represents independently for each occurrence hydrogen, alkyl, aryl, or aralkyl, wherein any two instances of $R^6$ may be covalently attached to form a ring;
X is S, —S(O)—, or —S(O$_2$)—;
n is 1, 2, 3, or 4; and
m is 1, 2, 3, or 4.

In certain embodiments, the present invention relates to compound I, wherein X is S or —S(O)—.

In certain embodiments, the present invention relates to compound I, wherein $R^2$ is methyl, ethyl or propyl.

In certain embodiments, the present invention relates to compound I, wherein $R^2$ is methyl.

In certain embodiments, the present invention relates to compound I, wherein $R^3$ is optionally substituted phenyl.

In certain embodiments, the present invention relates to compound I, wherein $R^3$ is halophenyl.

In certain embodiments, the present invention relates to compound I, wherein $R^3$ is 3-chlorophenyl.

In certain embodiments, the present invention relates to compound I, wherein $R^4$ is C(O)N($R^6$)$_2$.

In certain embodiments, the present invention relates to compound I, wherein $R^4$ is C(O)N($R^6$)$_2$ and $R^6$ represents independently for each occurrence hydrogen or alkyl.

In certain embodiments, the present invention relates to compound I, wherein X is S, n is 1, m is 1, $R^1$ is hydrogen, $R^2$ is methyl, and $R^3$ is 3-chlorophenyl.

In certain embodiments, the present invention relates to compound I, wherein X is S, n is 1, m is 1, $R^1$ is hydrogen, $R^2$ is methyl, $R^3$ is 3-chlorophenyl, and $R^4$ is C(O)N($R^6$)$_2$.

In certain embodiments, the present invention relates to compound I, wherein X is S, n is 1, m is 1, $R^1$ is hydrogen, $R^2$ is methyl, $R^3$ is 3-chlorophenyl, and $R^4$ is C(O)N(H)iPr.

In certain embodiments, the present invention relates to compound I, wherein X is S, n is 1, m is 1, $R^1$ is hydrogen, $R^2$ is methyl, $R^3$ is 3-chlorophenyl, and $R^4$ is C(O)N(H)CH$_3$.

In certain embodiments, the present invention relates to compound I, wherein X is —S(O)—, n is 1, $R^1$ is hydrogen, $R^2$ is methyl, and $R^3$ is 3-chlorophenyl.

In certain embodiments, the present invention relates to compound I, wherein X is —S(O)—, n is 1, m is 2, $R^1$ is hydrogen, $R^2$ is methyl, $R^3$ is 3-chlorophenyl, and $R^4$ is OC(O)$R^5$.

In certain embodiments, the present invention relates to compound I, wherein X is —S(O)—, n is 1, m is 2, $R^1$ is hydrogen, $R^2$ is methyl, $R^3$ is 3-chlorophenyl, $R^4$ is OC(O)$R^5$, and $R^5$ is CH$_3$.

In certain embodiments, the present invention relates to compound I, wherein X is —S(O)—, n is 1, m is 2, $R^1$ is hydrogen, $R^2$ is methyl, $R^3$ is 3-chlorophenyl, $R^4$ is OC(O)$R^5$, and $R^5$ is phenyl.

In certain embodiments, the present invention relates to compound I, wherein X is —S(O)— n is 1, m is 1, $R^1$ is hydrogen, $R^2$ is methyl, $R^3$ is 3-chlorophenyl, and $R^4$ is C(O)NHOH.

Importantly, the embodiments described above for the compound of formula I are also envisioned for the compounds of formulas II, III, IV, V, and VI listed below.

Another aspect of the present invention relates to a compound represented by formula II:

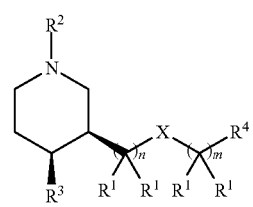

wherein
$R^1$ represents independently for each occurrence H or alkyl;
$R^2$ is H, alkyl, aryl, aralkyl, or —C(O)$R^5$;
$R^3$ is aryl, heteroaryl, or aralkyl;
$R^4$ is hydrogen, hydroxyl, aryl, heteroaryl, O$R^5$, CO$_2$$R^6$, C(O)N($R^6$)$_2$, C(O)NHOH, OC(O)$R^5$, or oxadiazole;
$R^5$ is alkyl, aryl, heteroaryl, or aralkyl;
$R^6$ represents independently for each occurrence hydrogen, alkyl, aryl, or aralkyl, wherein any two instances of $R^6$ may be covalently attached to form a ring;
X is S, —S(O)—, or —S(O$_2$)—;
n is 1, 2, 3, or 4; and
m is 1, 2, 3, or 4.

In certain embodiments, the present invention relates to compound II, wherein X is S or —S(O)—.

In certain embodiments, the present invention relates to compound H, wherein $R^2$ is methyl, ethyl or propyl.

In certain embodiments, the present invention relates to compound H, wherein $R^2$ is methyl.

In certain embodiments, the present invention relates to compound H, wherein $R^3$ is optionally substituted phenyl.

In certain embodiments, the present invention relates to compound H, wherein $R^3$ is halophenyl.

In certain embodiments, the present invention relates to compound H, wherein $R^3$ is 3-chlorophenyl.

In certain embodiments, the present invention relates to compound H, wherein $R^4$ is C(O)N(R)$_2$.

In certain embodiments, the present invention relates to compound H, wherein $R^4$ is C(O)N($R^6$)$_2$ and $R^6$ represents independently for each occurrence hydrogen or alkyl.

In certain embodiments, the present invention relates to compound H, wherein X is S, n is 1, m is 1, $R^1$ is hydrogen, $R^2$ is methyl, and $R^3$ is 3-chlorophenyl.

In certain embodiments, the present invention relates to compound H, wherein X is S, n is 1, m is 1, $R^1$ is hydrogen, $R^2$ is methyl, $R^3$ is 3-chlorophenyl, and $R^4$ is $C(O)N(R^6)_2$.

In certain embodiments, the present invention relates to compound H, wherein X is S, n is 1, m is 1, $R^1$ is hydrogen, $R^2$ is methyl, $R^3$ is 3-chlorophenyl, and $R^4$ is C(O)N(H)iPr.

Another aspect of the present invention relates to a compound represented by formula III:

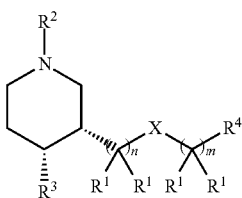

III wherein
$R^1$ represents independently for each occurrence H or alkyl;
$R^2$ is H, alkyl, aryl, aralkyl, or —$C(O)R^5$;
$R^3$ is aryl, heteroaryl, or aralkyl;
$R^4$ is hydrogen, hydroxyl, aryl, heteroaryl, $OR^5$, $CO_2R^6$, $C(O)N(R^6)_2$, C(O)NHOH, $OC(O)R^5$, or oxadiazole;
$R^5$ is alkyl, aryl, heteroaryl, or aralkyl;
$R^6$ represents independently for each occurrence hydrogen, alkyl, aryl, or aralkyl, wherein any two instances of $R^6$ may be covalently attached to form a ring;
X is S, —S(O)—, or —$S(O_2)$—;
n is 1, 2, 3, or 4; and
m is 1, 2, 3, or 4.

In certain embodiments, the present invention relates to compound III, wherein X is S or —S(O)—.

In certain embodiments, the present invention relates to compound III, wherein $R^2$ is methyl, ethyl or propyl.

In certain embodiments, the present invention relates to compound III, wherein $R^2$ is methyl.

In certain embodiments, the present invention relates to compound III, wherein $R^3$ is optionally substituted phenyl.

In certain embodiments, the present invention relates to compound III, wherein $R^3$ is halophenyl.

In certain embodiments, the present invention relates to compound III, wherein $R^3$ is 3-chlorophenyl.

In certain embodiments, the present invention relates to compound III, wherein $R^4$ is $C(O)N(R)_2$.

In certain embodiments, the present invention relates to compound III, wherein $R^4$ is $C(O)N(R^6)_2$ and $R^6$ represents independently for each occurrence hydrogen or alkyl.

In certain embodiments, the present invention relates to compound III, wherein X is S, n is 1, m is 1, $R^1$ is hydrogen, $R^2$ is methyl, and $R^3$ is 3-chlorophenyl.

In certain embodiments, the present invention relates to compound III, wherein X is S, n is 1, m is 1, $R^1$ is hydrogen, $R^2$ is methyl, $R^3$ is 3-chlorophenyl, and $R^4$ is $C(O)N(R^6)_2$.

In certain embodiments, the present invention relates to compound III, wherein X is S, n is 1, m is 1, $R^1$ is hydrogen, $R^2$ is methyl, $R^3$ is 3-chlorophenyl, and $R^4$ is C(O)N(H)iPr.

Another aspect of the present invention relates to a compound represented by formula IV:

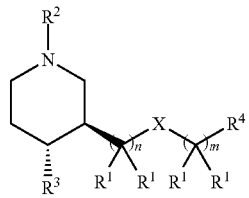

IV wherein
$R^1$ represents independently for each occurrence H or alkyl;
$R^2$ is H, alkyl, aryl, aralkyl, or —$C(O)R^5$;
$R^3$ is aryl, heteroaryl, or aralkyl;
$R^4$ is hydrogen, hydroxyl, aryl, heteroaryl, $OR^5$, $CO_2R^6$, $C(O)N(R^6)_2$, C(O)NHOH, $OC(O)R^5$, or oxadiazole;
$R^5$ is alkyl, aryl, heteroaryl, or aralkyl;
$R^6$ represents independently for each occurrence hydrogen, alkyl, aryl, or aralkyl, wherein any two instances of $R^6$ may be covalently attached to form a ring;
X is S, —S(O)—, or —$S(O_2)$—;
n is 1, 2, 3, or 4; and
m is 1, 2, 3, or 4.

In certain embodiments, the present invention relates to compound IV, wherein X is S or —S(O)—.

In certain embodiments, the present invention relates to compound IV, wherein $R^2$ is methyl, ethyl or propyl.

In certain embodiments, the present invention relates to compound IV, wherein $R^2$ is methyl.

In certain embodiments, the present invention relates to compound IV, wherein $R^3$ is optionally substituted phenyl.

In certain embodiments, the present invention relates to compound IV, wherein $R^3$ is halophenyl.

In certain embodiments, the present invention relates to compound IV, wherein $R^3$ is 3-chlorophenyl.

In certain embodiments, the present invention relates to compound IV, wherein $R^4$ is $C(O)N(R^6)_2$.

In certain embodiments, the present invention relates to compound IV, wherein $R^4$ is $C(O)N(R^6)_2$ and $R^6$ represents independently for each occurrence hydrogen or alkyl.

In certain embodiments, the present invention relates to compound IV, wherein X is S, n is 1, m is 1, $R^1$ is hydrogen, $R^2$ is methyl, and $R^3$ is 3-chlorophenyl.

In certain embodiments, the present invention relates to compound IV, wherein X is S, n is 1, m is 1, $R^1$ is hydrogen, $R^2$ is methyl, $R^3$ is 3-chlorophenyl, and $R^4$ is $C(O)N(R^6)_2$.

In certain embodiments, the present invention relates to compound IV, wherein X is S, n is 1, m is 1, $R^1$ is hydrogen, $R^2$ is methyl, $R^3$ is 3-chlorophenyl, and $R^4$ is C(O)N(H)iPr.

Another aspect of the present invention relates to a compound represented by formula V:

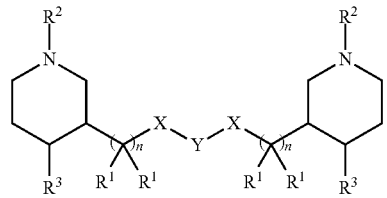

V wherein
- $R^1$ represents independently for each occurrence H or alkyl;
- $R^2$ is H, alkyl, aryl, aralkyl or —C(O)$R^4$;
- $R^3$ is aryl, heteroaryl, or aralkyl;
- $R^4$ is alkyl, aryl, heteroaryl, or aralkyl;
- X is S, —S(O)—, or —S(O$_2$)—;
- n represents independently for each occurrence 1, 2, 3, or 4; and
- Y is alkyl.

In certain embodiments, the present invention relates to compound V, wherein X is S or —S(O)—.

In certain embodiments, the present invention relates to compound V, wherein $R^2$ is methyl.

In certain embodiments, the present invention relates to compound V, wherein $R^3$ is optionally substituted phenyl.

In certain embodiments, the present invention relates to compound V, wherein $R^3$ is 3-chlorophenyl.

Another aspect of the present invention relates to a compound represented by formula VI:

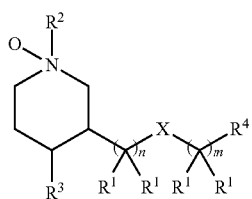

wherein
- $R^1$ represents independently for each occurrence H or alkyl;
- $R^2$ is H, alkyl, aryl, aralkyl, or —C(O)$R^5$;
- $R^3$ is aryl, heteroaryl, or aralkyl;
- $R^4$ is hydrogen, hydroxyl, aryl, heteroaryl, O$R^5$, CO$_2$$R^6$, C(O)N($R^6$)$_2$, C(O)NHOH, OC(O)$R^5$, or oxadiazole;
- $R^5$ is alkyl, aryl, heteroaryl, or aralkyl;
- $R^6$ represents independently for each occurrence hydrogen, alkyl, aryl, or aralkyl, wherein any two instances of $R^6$ may be covalently attached to form a ring;
- X is S, —S(O)—, or —S(O$_2$)—;
- n is 1, 2, 3, or 4; and
- m is 1, 2, 3, or 4.

In certain embodiments, the present invention relates to compound VI, wherein X is S or —S(O)—.

In certain embodiments, the present invention relates to compound VI, wherein $R^2$ is methyl, ethyl or propyl.

In certain embodiments, the present invention relates to compound VI, wherein $R^2$ is methyl.

In certain embodiments, the present invention relates to compound VI, wherein $R^3$ is optionally substituted phenyl.

In certain embodiments, the present invention relates to compound VI, wherein $R^3$ is halophenyl.

In certain embodiments, the present invention relates to compound VI, wherein $R^3$ is 3-chlorophenyl.

In certain embodiments, the present invention relates to compound VI, wherein $R^4$ is C(O)N($R^6$)$_2$.

In certain embodiments, the present invention relates to compound VI, wherein $R^4$ is C(O)N($R^6$)$_2$ and $R^6$ represents independently for each occurrence hydrogen or alkyl.

In certain embodiments, the present invention relates to compound VI, wherein X is S, n is 1, m is 1, $R^1$ is hydrogen, $R^2$ is methyl, and $R^3$ is 3-chlorophenyl.

In certain embodiments, the present invention relates to compound VI, wherein X is S, n is 1, m is 1, $R^1$ is hydrogen, $R^2$ is methyl, $R^3$ is 3-chlorophenyl, and $R^4$ is C(O)N($R^6$)$_2$.

In certain embodiments, the present invention relates to compound VI, wherein X is S, n is 1, m is 1, $R^1$ is hydrogen, $R^2$ is methyl, $R^3$ is 3-chlorophenyl, and $R^4$ is C(O)N(H)iPr.

In certain embodiments, the present invention relates to a compound of formula I, II, III, IV, V, or VI, wherein said compound has an EC$_{50}$ less than 1 μM in an assay based on a mammalian dopamine, serotonin, or norepinephrine receptor or transporter.

In certain embodiments, the present invention relates to a compound of formula I, II, III, IV, V, or VI, wherein said compound has an EC$_{50}$ less than 10 nM in an assay based on a mammalian dopamine, serotonin, or norepinephrine receptor or transporter.

In certain embodiments, the present invention relates to a compound of formula I, II, III, IV, V, or VI, wherein said compound has an EC$_{50}$ less than 100 nM in an assay based on a mammalian dopamine, serotonin, or norepinephrine receptor or transporter.

In certain embodiments, the present invention relates to a compound of formula I, II, III, IV, V, or VI, wherein said compound has an IC$_{50}$ less than 1 μM in an assay based on a mammalian dopamine, serotonin, or norepinephrine receptor or transporter.

In certain embodiments, the present invention relates to a compound of formula I, II, III, IV, V, or VI, wherein said compound has an IC$_{50}$ less than 10 nM in an assay based on a mammalian dopamine, serotonin, or norepinephrine receptor or transporter.

In certain embodiments, the present invention relates to a compound of formula I, II, III, IV, V, or VI, wherein said compound has an IC$_{50}$ less than 100 nM in an assay based on a mammalian dopamine, serotonin, or norepinephrine receptor or transporter.

Methods of Treatment

Another aspect of the invention relates to a method of modulating the activity of a dopamine, serotonin, or norepinephrine receptor or transporter in a mammal, comprising the step of:
administering to said mammal a therapeutically effective amount of a compound of formula I, II, III, IV, V, or VI.

In certain embodiments, the present invention relates to the aforementioned method, wherein said mammal is a primate, equine, canine or feline.

In certain embodiments, the present invention relates to the aforementioned method, wherein said mammal is a human.

In certain embodiments, the present invention relates to the aforementioned method, wherein said compound is administered orally.

In certain embodiments, the present invention relates to the aforementioned method, wherein said compound is administered intravenously.

In certain embodiments, the present invention relates to the aforementioned method, wherein said compound is administered sublingually.

In certain embodiments, the present invention relates to the aforementioned method, wherein said compound is administered ocularly.

In certain embodiments, the present invention relates to the aforementioned method, wherein said compound is administered transdermally.

In certain embodiments, the present invention relates to the aforementioned method, wherein said compound is administered rectally.

In certain embodiments, the present invention relates to the aforementioned method, wherein said compound is administered vaginally.

In certain embodiments, the present invention relates to the aforementioned method, wherein said compound is administered topically.

In certain embodiments, the present invention relates to the aforementioned method, wherein said compound is administered intramuscularly.

In certain embodiments, the present invention relates to the aforementioned method, wherein said compound is administered subcutaneously.

In certain embodiments, the present invention relates to the aforementioned method, wherein said compound is administered buccally.

In certain embodiments, the present invention relates to the aforementioned method, wherein said compound is administered nasally.

Another aspect of the present invention relates to a method of treating a mammal suffering from addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, or Tourette's syndrome, comprising the step of:

administering to said mammal a therapeutically effective amount of a compound of formula I, II, III, IV, V, or VI.

In certain embodiments, the present invention relates to the aforementioned method, wherein said mammal is a primate, equine, canine or feline.

In certain embodiments, the present invention relates to the aforementioned method, wherein said mammal is a human.

In certain embodiments, the present invention relates to the aforementioned method, wherein said compound is administered orally.

In certain embodiments, the present invention relates to the aforementioned method, wherein said compound is administered intravenously.

In certain embodiments, the present invention relates to the aforementioned method, wherein said compound is administered sublingually.

In certain embodiments, the present invention relates to the aforementioned method, wherein said compound is administered ocularly.

In certain embodiments, the present invention relates to the aforementioned method, wherein said compound is administered transdermally.

In certain embodiments, the present invention relates to the aforementioned method, wherein said compound is administered rectally.

In certain embodiments, the present invention relates to the aforementioned method, wherein said compound is administered vaginally.

In certain embodiments, the present invention relates to the aforementioned method, wherein said compound is administered topically.

In certain embodiments, the present invention relates to the aforementioned method, wherein said compound is administered intramuscularly.

In certain embodiments, the present invention relates to the aforementioned method, wherein said compound is administered subcutaneously.

In certain embodiments, the present invention relates to the aforementioned method, wherein said compound is administered buccally.

In certain embodiments, the present invention relates to the aforementioned method, wherein said compound is administered nasally.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 per cent to about ninety-nine percent of active ingredient, preferably from about 5 per cent to about 70 per cent, most preferably from about 10 per cent to about 30 per cent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and mono-unsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter .alpha., .beta. or .gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113

(1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (II), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C.sub.14 to about C.sub.20).

Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1, and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween™ and Pluronic™. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Combinatorial Libraries

The subject compounds may be synthesized using the methods of combinatorial synthesis described in this section. Combinatorial libraries of the compounds may be used for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811-5814; Valerio et al. (1991) *Anal Biochem* 197:168-177; Bray et al. (1991) *Tetrahedron Lett* 32:6163-6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131-5135; and U.S. Pat. Nos. 4,631,211; 5,440, 016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med*

*Chem* 26:271-280; Fodor, S. P. A. (1991) *Science* 251:767; Pirrung et al. (1992) U.S. Pat. No. 5,143,854; Jacobs et al. (1994) *Trends Biotechnol* 12:19-26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381-5383), and an example of such a library appeared the following year (Needles et al. (1993) *PNAS* 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529-2531), orthogonality in synthesis is achieved by employing acid-labile protection for the coding strand and base-labile protection for the compound strand.

In an alternative approach (Nikolaiev et al. (1993) *Pept Res* 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) *PNAS* 90:1.0922-10926). Exemplary tags are haloaromatic alkyl ethers, that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable O-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

(3R,4S)-4-(4-Chlorophenyl)-3-(hydroxymethyl)-1-methylpiperidine

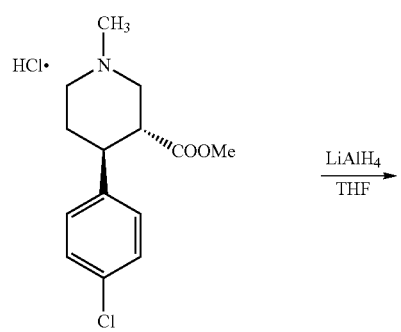

-continued

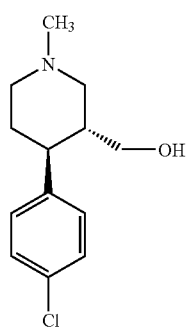

To a solution of (3R,4S)-4-(4-chlorophenyl)-1-methylpiperidine-3-carboxylic acid methyl ester (2.0 g, 6.57 mmol) in anhydrous THF (40 mL) that was cooled to 0° C. was added LiAlH$_4$ (374 mg, 9.86 mmol). The resulting mixture was warmed to room temperature and stirred overnight, then quenched with a saturated solution of NH$_4$Cl (30 mL). The mixed solution was extracted with CH$_2$Cl$_2$ (3×25 mL). The combined organic extract was dried over Na$_2$SO$_4$, concentrated and purified by column chromatography on silica gel with EtOAc/MeOH/Et$_3$N (8:1:1) as the eluent to yield the product as a white solid (1.45 g, 92%). $[\alpha]^{25}_D$ +27.1° (c 0.38, CHCl$_3$); $^1$H NMR (CDCl$_3$, 300 MHz), δ 1.69-1.82 (m, 2H), 1.87 (dd, J=10.5 and 10.8 Hz, 1H), 1.90-2.03 (m, 2H), 2.24 (td, J=6.3 and 10.1 Hz, 1H), 2.29 (s, 3H), 2.84-2.94 (m, 1H), 3.14 (dd, J=7.2 and 11.1 Hz, 2H), 3.34 (dd, J=2.7 and 11.0 Hz, 1H), 3.51 (brs, 1H), 7.09 (d, J=8.4 Hz, 2H), 7.22 (d, J=8.4 Hz, 2H); $^{13}$C NMR (CDCl$_3$, 75 MHz) δ 34.3, 43.9, 44.1, 46.6, 56.2, 59.5, 63.3, 128.8, 128.9, 132.1, 142.9; MS (EI), m/z (%) 239 (M$^+$, 11), 208 (12), 183 (3), 125 (8), 115 (14), 100 (100).

Example 2

(3R,4S)-4-(4-Chlorophenyl)-3-(iodomethyl)-1-methylpiperidine

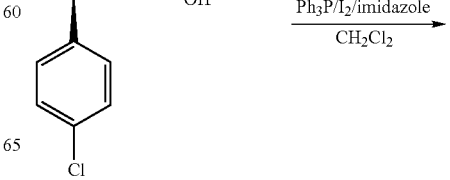

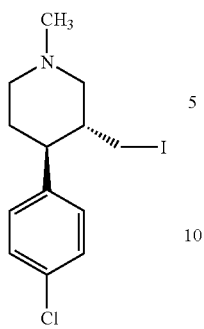

To a solution of PPh$_3$ (2.41 g, 9.18 mmol) in anhydrous CH$_2$Cl$_2$ (60 mL) was added iodine (2.33 g, 9.18 mmol) under nitrogen at room temperature. After stirring at room temperature for 15 min, imidazole (0.71 g, 10.43 mmol) was added in one portion, followed by the addition of the alcohol (1.0 g, 4.17 mmol) solution in 20 mL of CH$_2$Cl$_2$ at room temperature. The resulting mixture was then heated to reflux for 2.5 h. After cooling to room temperature, the reaction mixture washed with 5% sodium thiosulfate aqueous solution to remove the excess iodine. The organic phase was dried over Na$_2$SO$_4$, concentrated and purified by column chromatography on silica gel first with EtOAc as the eluent to remove all the formed triphenyl phosphate and then with EtOAc/Et$_3$N (98/2 to 95/5) as the eluent to provide the product as a colorless oil (1.25 g, 86%). $[\alpha]^{25}_D$ +56.40° (c 0.28, CHCl$_3$); $^1$H NMR (CDCl$_3$, 300 MHz) δ 1.66-1.82 (m, 2H), 1.84-2.01 (m, 2H), 2.08 (td, J=3.0 and 13.2 Hz, 1H), 2.29 (td, J=4.5 and 11.3 Hz, 1H), 2.38 (s, 3H), 2.75 (dd, J=6.9 and 10.1 Hz, 1H), 2.90-2.98 (m, 1H), 3.04 (dd, J=2.7 and 12.9 Hz, 1H), 3.08-3.17 (m, 1H), 7.17 (d, J=8.4 Hz, 2H), 7.28 (d, J=8.7 Hz, 2H); $^{13}$C NMR (CDCl$_3$, 75 MHz) δ 10.7, 33.8, 41.4, 46.1, 46.6, 55.9, 61.9, 128.8 (2 overlapped), 132.2, 141.4; MS (EI), m/z (%) 349 (M$^+$, 14), 222 (100), 151 (8), 125 (16), 115 (44). Anal. (C$_{13}$H$_{17}$ClIN.0.75H$_2$O)C, H, N.

Example 3

[(3R,4S)-4-(4-Chlorophenyl)-1-methyl-piperidin-3-ylmethlsulfanyl]-acetic Acid Methyl Ester

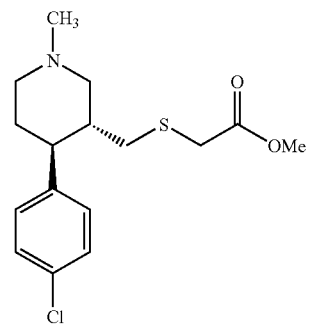

To a solution of the above iodide (617 mg, 1.76 mmol) in anhydrous MeCN (20 mL) was added 316 μL of methyl thioglycolate (374 mg, 3.52 mmol) under nitrogen at room temperature, followed by the addition of cesium carbonate (1.43 g, 4.40 mmol). After stirring at room temperature overnight, the solvent was evaporated and the residue was petitioned with CH$_2$Cl$_2$/H$_2$O (1/1, 40 mL). The aqueous layer was extracted with CH$_2$Cl$_2$ (3×25 mL), and the combined organic layers were dried over anhydrous sodium sulfate, filtered and concentrated under vacuum. The crude product was purified by column chromatography on a silica gel using a mixture of EtOAc/Et$_3$N (98/2 to 10/1) as the eluent to afford the product as a colorless oil (505 mg, 88%). R$_f$ [EtOAc/Et$_3$N (10/1)]=0.41 or R$_f$ [EtOAc/MeOH/Et$_3$N (8/1/1)]=0.63. $[\alpha]^{25}_D$ +97.8° (c 0.27, CHCl$_3$); $^1$H NMR (CDCl$_3$, 300 MHz) δ 1.74-1.84 (m, 3H), 1.96-2.28 (m, 4H), 2.34 (s, 3H), 2.50 (dd, J=2.4 and 7.5 Hz, 1H), 2.92-2.97 (m, 1H), 3.06 (q, J=14.7 and 18.0 Hz, 2H), 3.22-3.28 (m, 1H), 3.60 (s, 3H), 7.12 (d, J=8.4 Hz, 2H), 7.27 (d, J=8.7 Hz, 2H); $^{13}$C NMR (CDCl$_3$, 75 MHz) δ 33.7, 34.5, 34.7, 41.0, 46.3, 46.9, 52.1, 56.0, 60.6, 128.6, 128.8, 132.0, 142.2, 170.4; MS (EI), m/z (%) 327 (M$^+$, 14), 254 (100), 222 (42), 208 (33), 125 (19), 116 (40), 115 (37). Anal. (C$_{16}$H$_{22}$ClNO$_2$S.0.1H$_2$O)C, H, N.

Example 4

2-[(3R,4S)-4-(4-Chlorophenyl)-1-methyl-piperidin-3-ylmethlsulfanyl]-acetamide

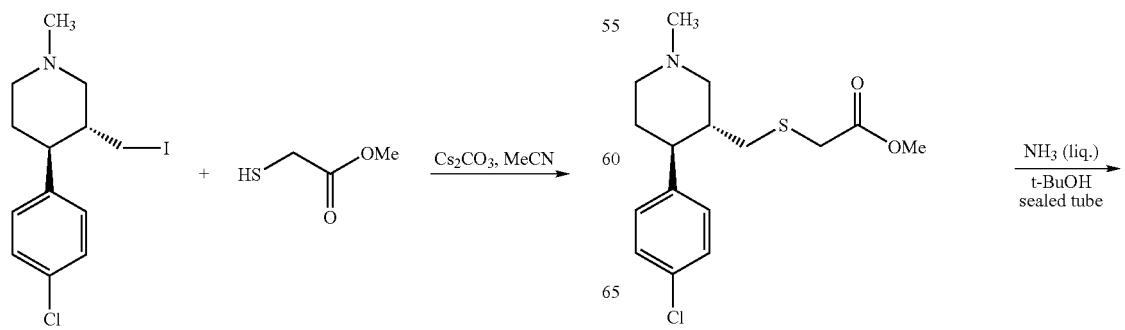

-continued

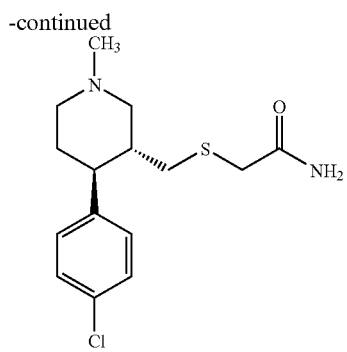 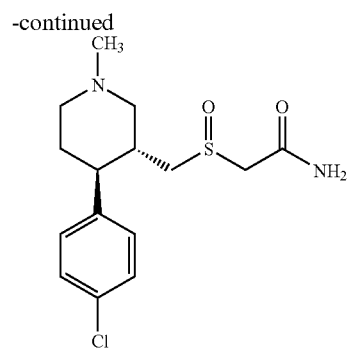

To a solution of [(3R,4S)-4-(4-chlorophenyl)-1-methyl-piperidin-3-ylmethylsulfanyl]-acetic acid methyl ester (176 mg, 0.54 mmol) in t-BuOH (3 mL) in a tube that was cooled with dry ice-acetone bath was introduced excess ammonium gas. Then the tube was sealed and the reaction mixture was stirred at room temperature for 72 h. The solvent was evaporated under vacuum. The crude product was purified by column chromatography on a silica gel using a mixture of EtOAc/MeOH/Et$_3$N (8/1/1) as the eluent to give the product as a white solid (160 mg, 95%). R$_f$ [EtOAc/MeOH/Et$_3$N (8/1/1)]=0.28. [α]$^{25}_D$ +104.8° (c 0.11, CHCl$_3$); $^1$H NMR (CDCl$_3$, 300 MHz) δ 1.74-1.86 (m, 3H), 1.96-2.28 (m, 4H), 2.35 (s, 3H), 2.42 (dd, J=2.1 and 12.0 Hz, 1H), 2.90-2.98 (m, 1H), 3.05 (q, J=16.5 and 22.1 Hz, 2H), 3.21-3.26 (m, 1H), 5.96 (brs, 1H), 6.47 (brs, 1H), 7.11 (d, J=8.7 Hz, 2H), 7.27 (d, J=8.7 Hz, 2H); $^{13}$C NMR (CDCl$_3$, 75 MHz) δ 34.6, 35.3, 36.3, 41.1, 46.3, 47.0, 56.0, 60.6, 128.8, 128.9, 132.3, 142.1, 171.3; MS (EI), m/z (%) 312 (M$^+$, 9), 254 (100), 222 (59), 208 (49), 151 (11), 128 (22), 125 (37), 116 (64), 115 (70), 103 (14). Anal. (C$_{15}$H$_{21}$ClN$_2$OS)C, H, N.

To a solution of 2-[(3R,4S)-4-(4-chlorophenyl)-1-methyl-piperidin-3-ylmethylsulfanyl]-acetamide (59 mg, 0.189 mmol) in acetic acid (2.0 mL) was added 19 μL of 35% H$_2$O$_2$ at room temperature. After stirring at room temperature for 2.5 h, the solvent was evaporated under vacuum. The crude product was purified by preparative TLC using a mixture of EtOAc/MeOH/Et$_3$N (8/1/1) as the developing solvent to afford the product as a white solid (43 mg, 69%). R$_f$ [EtOAc/MeOH/Et$_3$N (8/1/1)]=0.14. [α]$^{25}_D$ +72.2° (c 0.21, CHCl$_3$); $^1$H NMR (CDCl$_3$, 300 MHz) δ 1.80-1.96 (m, 2H), 1.98-2.22 (m, 3H), 2.26-2.41 (m, 1H), 2.38 (ds, 3H), 2.42-2.53 (m, 1H), 2.59-2.69 (m, 1H), 2.98-3.05 (m, 1H), 3.16 (dd, J=14.7 and 42.0 Hz, 1H), 3.27-3.40 (m, 1H), 3.53 (dd, J=9.9 and 14.1 Hz, 1H), 5.80 (d, J=8.1 Hz, 1H), 6.95 (d, J=11.4 Hz, 1H), 7.13 (dd, J=1.5 and 8.4 Hz, 2H), 7.29 (dd, J=1.5 and 8.4 Hz, 2H); $^{13}$C NMR (CDCl$_3$, 75 MHz) δ 33.8 and 34.0 (1C), 36.3 and 38.1 (1C), 45.6 (1C), 46.7 and 47.3 (1C), 53.6 and 53.8 (1C), 53.9 and 54.2 (1C), 55.3 and 55.4 (1C), 59.9 and 60.5 (1C), 128.9 and 129.0 (1C), 129.1 and 129.2 (1C), 132.7 and 132.8 (1C), 140.9 and 141.0 (1C), 165.8 and 165.9 (1C); MS (EI), m/z (%) 311 (M$^+$-17, 17), 270 (8), 220 (100), 186 (10), 129 (8), 115 (29). HRMS-FAB m/z [M+H]$^+$ calcd for C$_{15}$H$_{22}$ClN$_2$O$_2$S, 329.1091. found 329.1100. HPLC conditions are as follows: Column: Waters μ Bondapak C$_{18}$ 300× 7.8 mm; Flow rate: 2.8 mL/min; Detection at 280 nm; Gradient from 20% acetonitrile in water (0.05% CF$_3$COOH) to 90% acetonitrile in water (0.05% CF$_3$COOH) in 30 min; HPLC Purity: 100%; t$_R$=8.72 min. Anal. (C$_{15}$H$_{21}$ClN$_2$O$_2$S.0.7HCl) C, H, N.

Example 5

2-[(3R,4S)-4-(4-Chlorophenyl)-1-methyl-piperidin-3-ylmethanesulfinyl]-acetamide

Example 6

2-[(3R,4S)-4-(4-Chlorophenyl)-1-methyl-piperidin-3-ylmethanesulfinyl]-acetamide N-Oxide

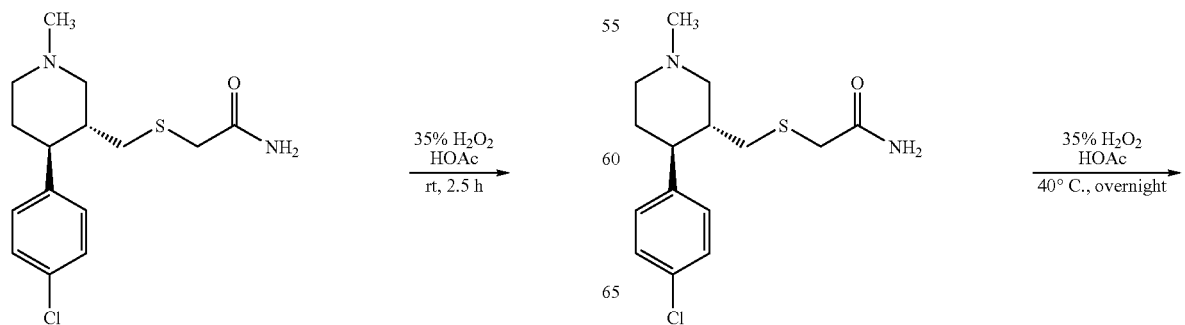

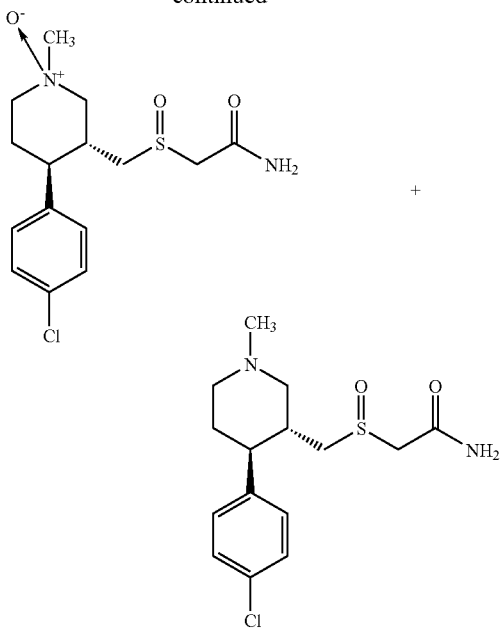

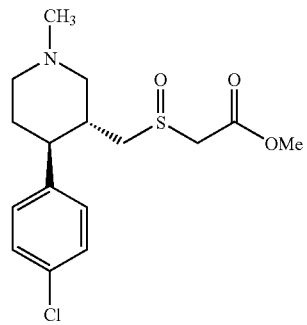

To a solution of [(3R,4S)-4-(4-chlorophenyl)-1-methyl-piperidin-3-ylmethylsulfanyl]-acetamide (28 mg, 0.0895 mmol) in acetic acid (1.0 mL) was added 20 μL of 35% $H_2O_2$ at 40° C. After stirring at this temperature overnight, the solvent was evaporated under vacuum. The crude product was purified by preparative TLC using a mixture of EtOAc/MeOH/$Et_3$N (8/1/1) as the developing solvent to afford the acetamide N-oxide as a white solid (10 mg, 32%) with $R_f$ [EtOAc/MeOH/$Et_3$N (8/1/1)]=0.46 and the acetamide (8 mg, 27%) with $R_f$ [EtOAc/MeOH/$Et_3$N (8/1/1)]=0.14. $[\alpha]^{25}_D$ +32.0° (c 0.08, $CH_3OH$); $^1$H NMR ($CDCl_3$ and $CD_3OD$, 300 MHz) δ 1.66-1.80 (m, 2H), 1.93 (dd, J=11.1 and 11.4 Hz, 1H), 1.98-2.05 (m, 1 H), 2.14-2.26 (m, 2H), 2.25 (s, 3H), 2.44-2.60 (m, 1H), 2.82-2.88 (m, 3H), 3.38-3.48 (m, 1H), 3.62 (dd, J=11.2 and 21.8 Hz, 1H), 7.03 (d, J=8.7 Hz, 2H), 7.17 (d, J=8.7 Hz, 2H); $^{13}$C NMR ($CDCl_3$, 75 MHz) δ 33.9, 35.3, 45.5, 46.3, 48.5, 54.1, 55.3, 60.2, 128.8, 128.9, 132.6, 140.4, 165.8; MS (EI), m/z (%) 344 ($M^+$, 7), 222 (100), 188 (10), 151 (7), 129 (12), 115 (46), 103 (10). HRMS-FAB m/z $[M+H]^+$ calcd for $C_{15}H_{22}ClN_2O_3S$, 345.1040. found 345.1040. Anal. ($C_{15}H_{21}ClN_2O_3S \cdot 0.33H_2O$) C, H, N.

Example 7

2-[(3R,4S)-4-(4-Chlorophenyl)-1-methyl-piperidin-3-ylmethanesulfinyl]-acetic Acid Methyl Ester To a solution of [(3R,4S)-4-(4-chlorophenyl)-1-methyl-piperidin-3-ylmethylsulfanyl]-acetic acid methyl ester (44 mg, 0.134 mmol) in acetic acid (2.0 mL) was added 14 μL of 35% $H_2O_2$ at room temperature. After stirring at room temperature for 2.5 h, the solvent was evaporated under vacuum. The crude product was purified by preparative TLC using a mixture of EtOAc/$Et_3$N (10/1) as the developing solvent to afford the product as a white solid (37 mg, 80%). $R_f$ [EtOAc/$Et_3$N (10/1)]=0.21. $[\alpha]^{25}_D$ +67.8° (c 0.80, $CHCl_3$); $^1$H NMR ($CDCl_3$, 300 MHz) δ 1.80-1.94 (m, 2H), 1.96-2.14 (m, 3H), 2.26-2.41 (m, 1H), 2.35 (ds, 3H), 2.46-2.66 (m, 2H), 2.94-3.04 (m, 1H), 3.26-3.36 (m, 1H), 3.40-3.64 (m, 2H), 3.67 (ds, 3H), 7.13 (dd, J=1.2 and 8.4 Hz, 2H), 7.29 (dd, J=1.5 and 8.4 Hz, 2H); $^{13}$C NMR ($CDCl_3$, 75 MHz) δ 34.2 and 34.7 (1C), 36.7 and 39.1 (1C), 46.1 (1C), 47.1 and 47.5 (1C), 52.8 (1C), 55.6 and 55.7 (1C), 55.8 and 55.9 (1C), 56.1 and 56.4 (1C), 60.4 and 61.1 (1C), 129.0 (1C), 129.1 (1C), 132.6 and 132.7 (1C), 141.3 and 141.4 (1C), 165.1 and 165.3 (1C); MS (EI), m/z (%) 326 ($M^+$-17, 48), 270 (9), 238 (11), 220 (100), 188 (19), 128 (14), 125 (20), 115 (48), 103 (12). HRMS-FAB m/z $[M+H]^+$ calcd for $C_{16}H_{23}ClNO_3S$, 344.1087. found 344.1093. Anal. ($C_{16}H_{22}ClNO_3S \cdot 0.5H_2O$) C, H, N.

Example 8

2-[(3R,4S)-4-(4-Chlorophenyl)-1-methyl-piperidin-3-ylmethlsulfanyl]-N-hydroxy-acetamide

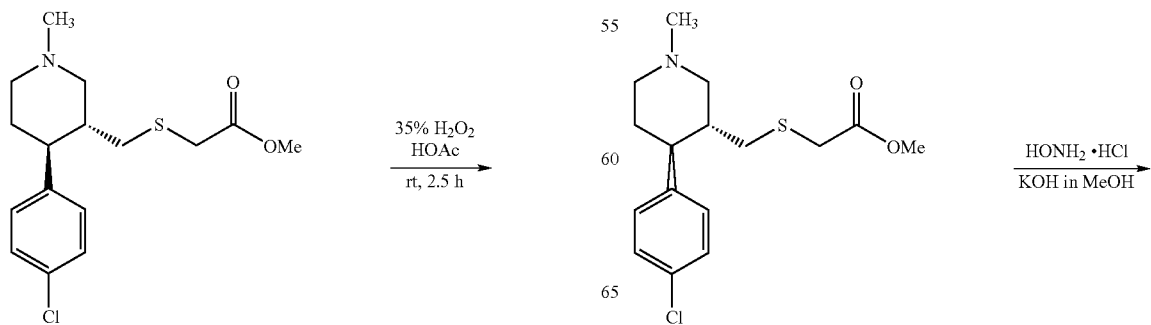

-continued

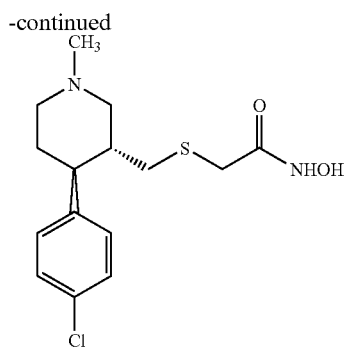

-continued

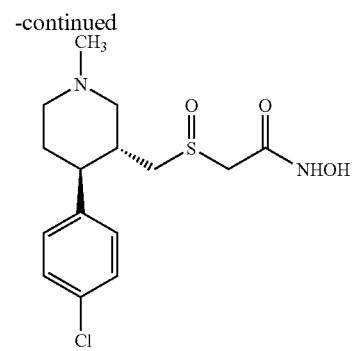

A solution of potassium hydroxide in methanol was made by dissolving 766 mg (13.68 mmol) of KOH in 5.0 mL of MeOH. To a solution of hydroxylamine hydrogen chloride (41.5 mg, 0.598 mmol) in 2.0 mL MeOH that was cooled to 5-10° C. was added 388 μL of above methanol solution of potassium hydroxide (59.4 mg, 1.06 mmol), followed by the addition of a solution of [(3R,4S)-4-(4-chlorophenyl)-1-methyl-piperidin-3-ylmethylsulfanyl]-acetic acid methyl ester (98 mg, 0.299 mmol) in MeOH (2.0 mL). Then the reaction mixture was stirred at room temperature for 2 h. The precipitate was filtered off and rinsed with $CH_2Cl_2$. The solvent of the combined organics was evaporated under vacuum. The crude product was purified by preparative TLC using a mixture of $EtOAc/MeOH/Et_3N$ (6/2/2) as the developing solvent to afford a colorless oil, which was further purified by HPLC (75 mg, 76%). $R_f[EtOAc/MeOH/Et_3N (6/2/2)]=0.18$. $[\alpha]^{25}_D$ +27.8° (c 0.37, $CH_3OH$); $^1H$ NMR ($CD_3OD$, 300 MHz) δ 1.86-2.08 (m, 2H), 2.26-2.44 (m, 2H), 2.54-2.72 (m, 2H), 2.88-3.01 (m, 2H), 2.96 (s, 3H), 3.03-3.24 (m, 2H), 3.54-3.64 (m, 1H), 3.86-3.93 (m, 1H), 7.24 (d, J=8.7 Hz, 2H), 7.35 (d, J=8.1 Hz, 2H); $^{13}C$ NMR ($CD_3OD$, 75 MHz) δ 33.0, 34.0, 34.9, 40.6, 44.4, 45.7, 55.8, 59.0, 130.4 (2C overlapped), 134.3, 141.5, 169.4; MS (EI), m/z (%) 254 (100), 222 (49), 220 (27), 208 (44), 151 (11), 128 (20), 125 (24), 116 (51), 115 (67), 103 (25). HRMS-FAB m/z $[M+H]^+$ calcd for $C_{15}H_{22}ClN_2O_2S$, 329.1091. found 329.1111. HPLC conditions are as follows: Column: Waters μ Bondapak $C_{18}$ 300× 7.8 mm; Flow rate: 2.8 mL/min; Detection at 280 nm; Gradient from 20% acetonitrile in water (0.05% $CF_3COOH$) to 80% acetonitrile in water (0.05% $CF_3COOH$) in 30 min; HPLC Purity: 99%; $t_R$=10.78 min.

Example 9

2-[(3R,4S)-4-(4-Chlorophenyl)-1-methyl-piperidin-3-ylmethanesulfinyl]-N-hydroxy-acetamide To a solution of 2-[(3R,4S)-4-(4-chlorophenyl)-1-methyl-piperidin-3-ylmethylsulfanyl]-N-hydroxy-acetamide (33 mg, 0.10 mmol) in acetic acid (1.0 mL) was added 10 μL of 35% $H_2O_2$ at room temperature. After stirring at room temperature for 2 h, the solvent was evaporated under vacuum. The crude product was purified by preparative TLC using a mixture of $EtOAc/MeOH/Et_3N/NH_3·H_2O$ (60/19/19/2) as the developing solvent to afford a colorless oil, which was further purified by HPLC (22 mg, 64%). $R_f[EtOAc/MeOH/Et_3N/NH_3·H_2O (60/19/19/2)]=0.16$. $[\alpha]^{25}_D$ +35.4° (c 0.31, $CH_3OH$); $^1H$ NMR ($CD_3OD$, 300 MHz) δ 1.98-2.18 (m, 2H), 2.62-2.90 (m, 4H), 2.96 (ds, 3H), 3.04-3.22 (m, 2H), 3.39 (dd, J=11.1 and 13.7 Hz, 1H), 3.58 (dd, J=10.2 and 13.4 Hz, 1H), 3.57-3.68 (m, 1H), 3.80-3.94 (m, 1H), 7.27 (dd, J=3.6 and 8.7 Hz, 2H), 7.37 (dd, J=2.7 and 8.4 Hz, 2H); $^{13}C$ NMR ($CD_3OD$, 75 MHz) δ 32.8 and 33.1 (1C), 36.4 and 38.1 (1C), 44.4 (1C), 45.3 and 46.1 (1C), 54.6 and 54.7 (1C), 55.5 and 55.7 (1C), 55.7 and 56.0 (1C), 58.4 and 59.2 (1C), 130.4 and 130.5 (1C), 130.6 and 130.7 (1C), 134.7 and 134.8 (1C), 140.8 and 140.9 (1C), 162.3 and 163.0 (1C); MS (EI), m/z (%) 327 ($M^+$-17, 3), 312 (8), 268 (43), 254 (50), 238 (16), 220 (99), 208 (26), 206 (21), 151 (13), 130 (54), 125 (41), 115 (100), 103 (25). HRMS-FAB m/z $[M+H]^+$ calcd for $C_{15}H_{22}ClN_2O_3S$, 345.1040. found 345.1059. HPLC conditions are as follows: Column: Waters μ Bondapak $C_{18}$ 300×7.8 mm; Flow rate: 2.8 mL/min; Detection at 280 nm; Gradient from 20% acetonitrile in water (0.05% $CF_3COOH$) to 50% acetonitrile in water (0.05% $CF_3COOH$) in 30 min; HPLC Purity: 98.4%; $t_R$=10.15 min.

Example 10

2-[(3R,4S)-4-(4-Chlorophenyl-1-methyl-piperidin-3-ylmethylsulfanyl]-ethanol

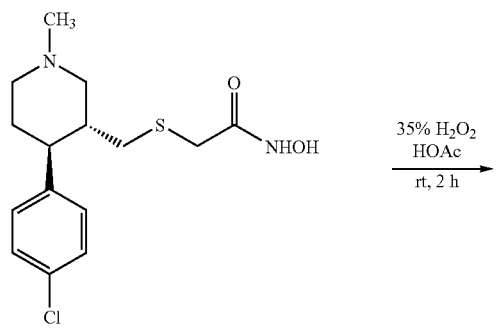

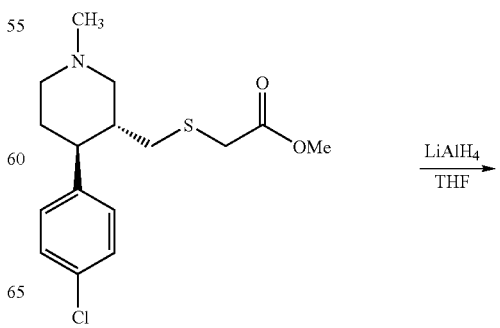

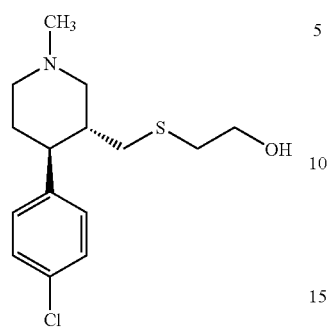

To a solution of [(3R,4S)-4-(4-chlorophenyl)-1-methyl-piperidin-3-ylmethylsulfanyl]-acetic acid methyl ester (271 mg, 0.827 mmol) in anhydrous THF (10 mL) that was cooled to 0° C. was added LiAlH$_4$ (47.1 mg, 1.24 mmol). The resulting mixture was warmed to room temperature and stirred overnight, then quenched with a saturated solution of NH$_4$Cl (10 mL). The mixed solution was extracted with CH$_2$Cl$_2$ (3×25 mL). The combined organic extract was dried over Na$_2$SO$_4$, concentrated and purified by column chromatography on silica gel with EtOAc/Et$_3$N (10:1) to EtOAc/MeOH/Et$_3$N (8:1:1) as the eluent to yield the product as a colorless oil (203 mg, 82%). R$_f$ [EtOAc/Et$_3$N (10/1)]=0.27. [α]$^{25}_D$ +81.6° (c 0.26, CHCl$_3$); $^1$H NMR (CDCl$_3$, 300 MHz) δ 1.64-1.80 (m, 3H), 1.90-2.04 (m, 3H), 2.12-2.32 (m, 1H), 2.25 (s, 3H), 2.29-2.36 (m, 1H), 2.46 (t, J=5.4 Hz, 2H), 2.82-2.87 (m, 1H), 3.17-3.22 (m, 1H), 3.14-3.52 (m, 2H), 3.70 (brs, 1H), 7.04 (d, J=8.7 Hz, 2H), 7.18 (d, J=8.4 Hz, 2H); $^{13}$C NMR (CDCl$_3$, 75 MHz) δ 33.9, 34.1, 35.5, 41.2, 46.1, 46.7, 55.9, 60.1, 60.4, 128.6, 128.7, 132.0, 142.2; MS (EI), m/z (%) 299 (M$^+$, 27), 254 (100), 222 (72), 208 (99), 188 (14), 174 (22), 125 (31), 115 (64), 111 (31). Anal. (C$_{15}$H$_{22}$ClNOS.0.2H$_2$O) C, H, N.

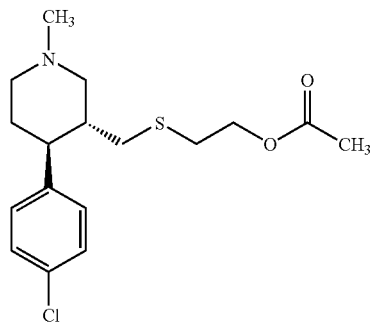

To a solution of the above alcohol (92 mg, 0.307 mmol) in pyridine (8 mL) was added 2.0 mL of Ac$_2$O under nitrogen at room temperature, followed by the addition of 1.0 mg of DMAP. After stirring at room temperature for 2 h, the solvent was evaporated and the residue was diluted with ethyl acetate and washed with the saturated NaHCO$_3$ aqueous solution (2×15 mL), and the organic layer was dried over anhydrous sodium sulfate, filtered and concentrated under vacuum. The crude product was purified by preparative TLC using a mixture of EtOAc/Et$_3$N (10/1) as the developing solvent to afford a colorless oil (74 mg, 70%). R$_f$ [EtOAc/Et$_3$N (10/1)]=0.57. [α]$^{25}_D$ +83.0° (c 0.54, CHCl$_3$); $^1$H NMR (CDCl$_3$, 300 MHz) δ 1.73-1.83 (m, 3H), 1.96-2.10 (m, 3H), 2.01 (s, 3H), 2.18-2.30 (m, 1H), 2.34 (s, 3H), 2.42 (dd, J=1.5 and 10.2 Hz, 1H), 2.56 (t, J=6.9 Hz, 2H), 2.90-2.96 (m, 1H), 3.23-3.29 (m, 1H), 3.96-4.08 (m, 2H), 7.13 (d, J=8.4 Hz, 2H), 7.27 (d, J=8.4 Hz, 2H); $^{13}$C NMR (CDCl$_3$, 75 MHz) δ 21.0, 31.2, 34.8 (2C overlapped), 41.8, 46.6, 47.2, 56.3, 60.9, 63.5, 129.0, 129.1, 132.4, 142.7, 170.9; MS (EI), m/z (%) 341 (M$^+$, 11), 282 (15), 254 (84), 222 (100), 208 (39), 188 (10), 151 (13), 125 (43), 115 (90), 111(34), 103 (24). Anal. (C$_{17}$H$_{24}$ClNO$_2$S.0.5HCl) C, H, N.

Example 11

Acetic Acid 2-[(3R,4S)-4-(4-Chlorophenyl-1-methyl-piperidin-3-ylmethlsulfanyl]-ethyl Ester Example 12

Acetic Acid 2-[(3R,4S)-4-(4-Chlorophenyl)-1-methyl-piperidin-3-ylmethanesulfinyl]-ethyl Ester

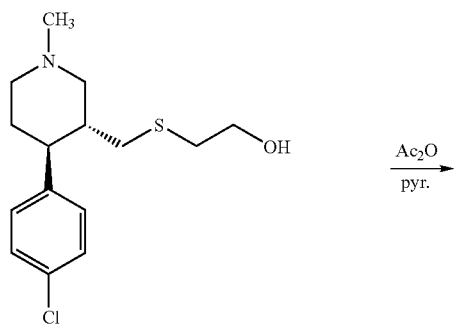

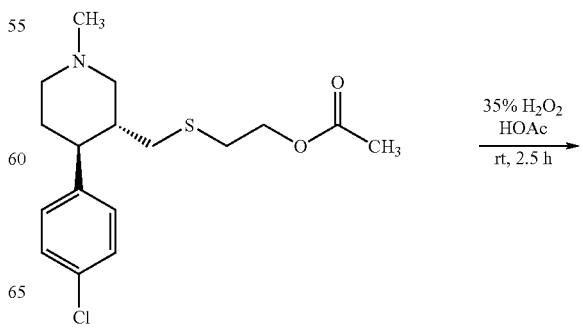

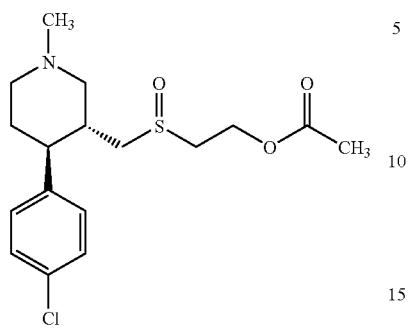

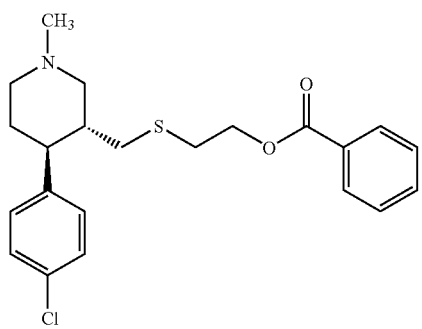

To a solution of the above ester (28 mg, 0.0819 mmol) in acetic acid (1.0 mL) was added 9 μL of 35% $H_2O_2$ at room temperature. After stirring at room temperature for 2.5 h, the solvent was evaporated under vacuum. The crude product was purified by preparative TLC using a mixture of $EtOAc/Et_3N$ (10/1) as the developing solvent to afford the product as a colorless oil (18 mg, 82%) and 7.0 mg of starting material was recovered. $R_f$ [EtOAc/$Et_3N$ (10/1)]=0.17. $[α]^{25}_D$ +74.0° (c 0.27, $CHCl_3$); $^1$H NMR ($CDCl_3$, 300 MHz) δ 1.80-1.87 (m, 2H), 1.89-2.12 (m, 3H), 2.01 (s, 3H), 2.20-2.38 (m, 1H), 2.35 (s, 3H), 2.43-2.64 (m, 2H), 2.68-2.80 (m, 2H), 2.94-2.99 (m, 1H), 3.31-3.36 (m, 1H), 4.28-4.48 (m, 2H), 7.12 (d, J=8.4 Hz, 2H), 7.28 (dd, J=2.7 and 8.4 Hz, 2H); $^{13}$C NMR ($CDCl_3$, 75 MHz) δ 20.9 (1C), 34.5 and 35.1 (1C), 37.0 and 39.4 (1C), 46.4 and 46.5 (1C), 47.5 and 47.9 (1C), 51.9 and 52.1 (1C), 55.8 and 56.0 (1C), 56.1 (1C), 57.1 and 57.3 (1C), 60.8 and 61.5 (1C), 129.1 (1C), 129.2 and 129.3 (1C), 132.8 and 132.9 (1C), 141.7 and 141.8 (1C), 170.7 (1C); MS (EI), m/z (%) 340 ($M^+$-17, 97), 238 (52), 220 (100), 202 (56), 151 (13), 125 (42), 115 (86), 103 (51). Anal. ($C_{17}H_{24}ClNO_3S·6H_2O$) C, H, N.

To a solution of the above alcohol (89 mg, 0.297 mmol) in anhydrous THF (8 mL) were added 83 μL of $Et_3N$ and 1.0 mg of DMAP under nitrogen at 0° C., followed by the addition of 52 μL of benzoyl chloride (62.5 mg, 0.445 mmol). After stirring at 0° C. to room temperature overnight, the solvent was evaporated and the residue was diluted with ethyl acetate and washed with the saturated $NaHCO_3$ aqueous solution (2×10 mL), and the organic layer was dried over anhydrous sodium sulfate, filtered and concentrated under vacuum. The crude product was purified by preparative TLC using a mixture of EtOAc/$Et_3N$ (10/1) as the developing solvent to afford a colorless oil (81 mg, 68%). $R_f$ [EtOAc/$Et_3N$ (10/1)]=0.51. $[α]^{25}_D$ +63.7° (c 0.33, $CHCl_3$); $^1$H NMR ($CDCl_3$, 300 MHz) δ 1.68-1.81 (m, 3H), 1.88-2.20 (m, 4H), 2.27 (s, 3H), 2.39 (dd, J=2.1 and 12.3 Hz, 1H), 2.63 (t, J=6.6 Hz, 2H), 2.84-2.87 (m, 1H), 3.17-3.22 (m, 1H), 4.16-4.28 (m, 2H), 7.05 (d, J=8.7 Hz, 2H), 7.18 (d, J=8.1 Hz, 2H), 7.34-7.39 (m, 2H), 7.46-7.52 (m, 1H), 7.91-7.96 (m, 2H); $^{13}$C NMR ($CDCl_3$, 75 MHz) δ 31.5, 34.8, 34.9, 41.9, 46.6, 47.2, 56.4, 60.9, 63.9, 128.6, 129.0 (2C overlapped), 129.8, 130.2, 132.4, 133.3, 142.7, 166.4; MS (EI), m/z (%) 403 ($M^+$, 2), 282 (14), 254 (74), 220 (100), 208 (33), 188 (40), 174 (15), 125 (20), 115 (45), 105 (92). Anal. ($C_{22}H_{26}ClNO_2S·2/3H_2O$) C, H, N.

Example 13

Benzoic Acid 2-[(3R,4S)-4-(4-Chlorophenyl)-1-methyl-piperidin-3-ylmethylsulfanyl]-ethyl Ester Example 14

Benzoic Acid 2-[(3R,4S)-4-(4-Chlorophenyl)-1-methyl-piperidin-3-ylmethanesulfinyl]-ethyl Ester

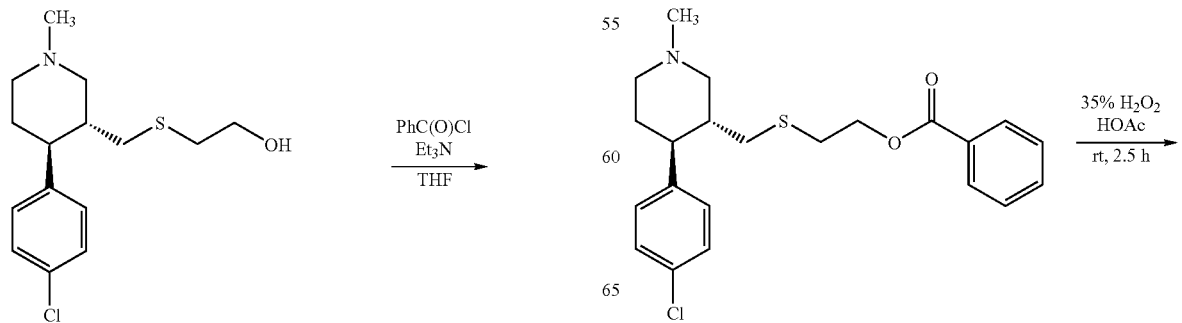

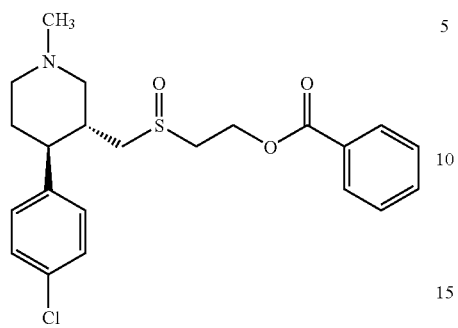

To a solution of the above ester (56 mg, 0.139 mmol) in acetic acid (2.0 mL) was added 14 µL of 35% $H_2O_2$ at room temperature. After stirring at room temperature for 2.5 h, the solvent was evaporated under vacuum. The crude product was purified by preparative TLC using a mixture of $EtOAc/Et_3N$ (10/1) as the developing solvent to afford the product as a colorless oil (45 mg, 77%). $R_f$ [$EtOAc/Et_3N$ (10/1)]=0.17. $[\alpha]^{25}_D$ +66.5° (c 0.43, $CHCl_3$); $^1H$ NMR ($CDCl_3$, 300 MHz) δ 1.74-1.82 (m, 2H), 1.87-2.02 (m, 2H), 2.27 (s, 3H), 2.21-2.34 (m, 2H), 2.36-2.55 (m, 2H), 2.71-2.92 (m, 3H), 3.22-3.28 (m, 1H), 4.46-4.68 (m, 2H), 7.04 (dd, J=2.7 and 8.7 Hz, 2H), 7.17 (dd, J=5.4 and 8.1 Hz, 2H), 7.36-7.42 (m, 2H), 7.48-7.58 (m, 1H), 7.90-7.96 (m, 2H); $^{13}C$ NMR ($CDCl_3$, 75 MHz) δ 34.5 and 35.0 (1C), 37.0 and 39.3, (1C), 46.4 (1C), 47.4 and 47.8 (1C), 52.3 and 52.4 (1C), 55.8 and 55.9 (1C), 56.0 and 56.1 (1C), 57.5 and 57.8 (1C), 60.8 and 61.4 (1C), 128.7 (1C), 129.1 (1C), 129.2 and 129.3 (1C), 129.6 (1C), 129.9 (1C), 132.8 and 132.9 (1C), 133.5 and 133.6 (1C), 141.6 and 141.7 (1C), 166.2 (1C); MS (EI), m/z (%) 402 ($M^+$-17, 8), 238 (18), 220 (42), 206 (8), 149 (12), 125 (13), 115 (22), 105 (100). Anal. ($C_{22}H_{26}ClNO_3S \cdot 0.8H_2O$) C, H, N.

Example 15

2-[(3R,4S)-4-(4-Chlorophenyl)-1-methyl-piperidin-3-ylmethanesulfinyl]-ethanol

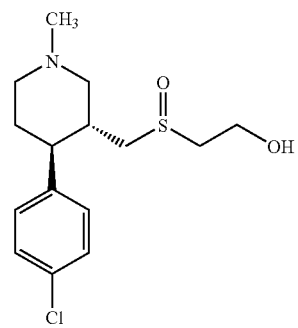

To a solution of the above alcohol (63 mg, 0.21 mmol) in acetic acid (2.0 mL) was added 20.8 µL of 35% $H_2O_2$ at room temperature. After stirring at room temperature for 2.5 h, the solvent was evaporated under vacuum. The crude product was purified by preparative TLC using a mixture of $EtOAc/MeOH/Et_3N$ (8/1/1) as the developing solvent to afford the product as a colorless oil (46 mg, 69%). $R_f$ [$EtOAc/MeOH/Et_3N$ (8/1/1)]=0.26. $[\alpha]^{25}_D$ +74.4° (c 0.31, $CHCl_3$); $^1H$ NMR ($CDCl_3$, 300 MHz) δ 1.72-1.84 (m, 2H), 1.89-2.09 (m, 2H), 2.29 (ds, 3H), 2.19-2.35 (m, 2H), 2.38-2.56 (m, 2H), 2.58-2.67 (m, 1H), 2.69-2.87 (m, 1H), 2.88-2.96 (m, 1H), 3.26-3.36 (m, 1H), 3.84-4.01 (m, 2H), 4.39 (brs, 1H), 7.06 (dd, J=2.1 and 8.7 Hz, 2H), 7.22 (dd, J=3.0 and 8.4 Hz, 2H); $^{13}C$ NMR ($CDCl_3$, 75 MHz) δ 34.2 and 34.6 (1C), 36.7 and 38.9 (1C), 46.2 and 46.3 (1C), 47.2 and 47.6 (1C), 54.8 (1C), 55.5 and 55.7 (1C), 55.8 and 55.9 (1C), 56.0 and 56.1 (1C), 60.6 and 61.1 (1C), 129.1 and 129.2 (1C), 129.3 (1C), 132.8 and 132.9 (1C), 141.4 and 141.5 (1C); MS (EI), m/z (%) 298 ($M^+$-17, 100), 264 (12), 238 (38), 220 (70), 206 (18), 160 (55), 125 (28), 115 (52), 103 (10). Anal. ($C_{15}H_{22}ClNO_2S \cdot 3/4HCl$) C, H, N.

Example 16

(3R,4S)-4-(4-Chlorophenyl)-3-(2-methoxyethylsulfanylmethyl)-1-methyl-piperidine

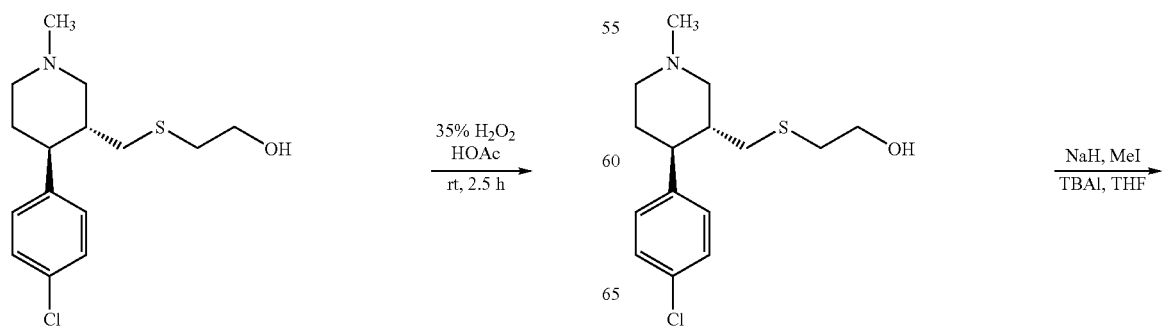

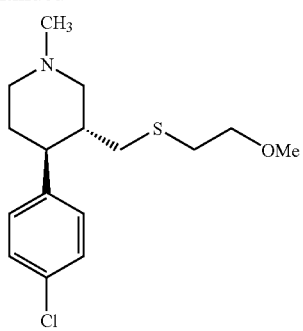

To a solution of the above alcohol (153 mg, 0.51 mmol) in anhydrous THF (6 mL) was added NaH (43 mg, 57-63% suspension in oil, 1.02 mmol) under nitrogen at 0° C. After stirring the mixture for 10 min, MeI (38.1 µL, 0.61 mmol) was added dropwise, followed by the addition of tetra-n-butylammonium iodide (19 mg, 0.051 mmol). After stirring at room temperature overnight, the reaction was quenched with NH$_4$Cl aqueous solution and the mixture was extracted with EtOAc (3×25 mL). The combined extracts were washed with 5% sodium thiosulfate aqueous solution and dried over anhydrous sodium sulfate, filtered and concentrated under vacuum. The crude product was purified by column chromatography on a silica gel using a mixture of EtOAc/Et$_3$N (98/2 to 10/1) as the eluent to afford the product as a colorless oil (104 mg, 65%). R$_f$ [EtOAc/Et$_3$N (10/1)]=0.44 or R$_f$ [EtOAc/MeOH/Et$_3$N (8/1/1)]=0.68. $[\alpha]^{25}_D$+84.6° (c 0.46, CHCl$_3$); $^1$H NMR (CDCl$_3$, 300 MHz) δ 1.65-1.76 (m, 3H), 1.88-2.05 (m, 3H), 2.13-2.23 (m, 1H), 2.27 (s, 3H), 2.34 (dd, J=1.8 and 12.0 Hz, 1H), 2.44 (t, J=6.6 Hz, 2H), 2.82-2.91 (m, 1H), 3.19 (s, 3H), 3.22-3.34 (m, 3H), 7.05 (d, J=8.7 Hz, 2H), 7.20 (d, J=8.7 Hz, 2H); $^{13}$C NMR (CDCl$_3$, 75 MHz) δ 32.1, 34.7 (2C overlapped), 41.8, 46.6, 47.1, 56.3, 58.8, 60.9, 71.9, 128.9, 129.1, 132.2, 142.8; MS (EI), m/z (%) 313 (M$^+$, 28), 254 (81), 222 (65), 208 (100), 125 (32), 116 (56), 111 (28). Anal. (C$_{16}$H$_{24}$ClNOS.1/5HCl) C, H, N.

Example 17

(3R,4S)-4-(4-Chlorophenyl-3-(2-methoxyethanesulfinylmethyl)-1-methyl-piperidine

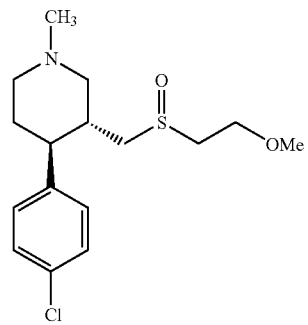

To a solution of the above ether (56 mg, 0.178 mmol) in acetic acid (2.0 mL) was added 17.6 mL of 35% H$_2$O$_2$ at room temperature. After stirring at room temperature for 2.5 h, the solvent was evaporated under vacuum. The crude product was purified by preparative TLC using a mixture of EtOAc/Et$_3$N (10/1) as the developing solvent to afford the product as a colorless oil (36 mg, 61%). R$_f$ [EtOAc/Et$_3$N (10/1)]=0.28. $[\alpha]^{25}_D$ +80.8° (c 0.37, CHCl$_3$); $^1$H NMR (CDCl$_3$, 300 MHz) δ 1.72-1.82 (m, 2H), 1.84-2.04 (m, 2H), 2.27 (s, 3H), 2.18-2.30 (m, 2H), 2.38-2.78 (m, 4H), 2.84-2.94 (m, 1H), 3.20 (ds, 3H), 3.24-3.32 (m, 1H), 3.52-3.68 (m, 2H), 7.06 (dd, J=1.8 and 8.4 Hz, 2H), 7.21 (dd, J=1.8 and 8.4 Hz, 2H); $^{13}$C NMR (CDCl$_3$, 75 MHz) δ 34.5 and 35.0 (1C), 37.0 and 39.6 (1C), 46.4 and 46.5 (1C), 47.4 and 47.7 (1C), 53.2 and 53.3 (1C), 55.7 and 56.0 (1C), 56.0 and 56.1 (1C), 59.1 (1C), 60.8 and 61.4 (1C), 64.7 and 64.9 (1C), 129.1 and 129.2 (1C), 129.2 and 129.3 (1C), 132.6 and 132.7 (1C), 141.8 and 141.9 (1C); MS (EI), m/z (%) 312 (M$^+$-17, 100), 278 (30), 238 (41), 220 (93), 206 (17), 186 (29), 174 (32), 125 (19), 115 (40). Anal. (C$_{16}$H$_{24}$ClNO$_2$S.1/3HCl) C, H, N.

Example 18

(3R,4S)-[4-(4-Chlorophenyl)-1-methyl-piperidin-3-ylmethlsulfanyl]-acetic acid

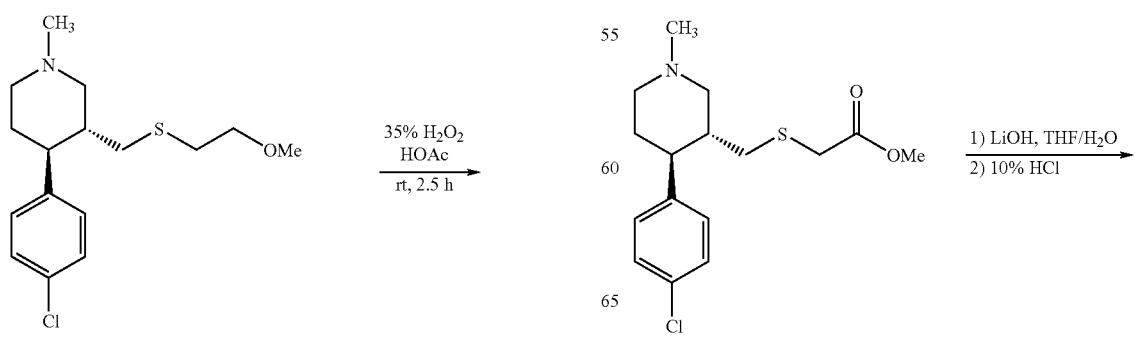

-continued

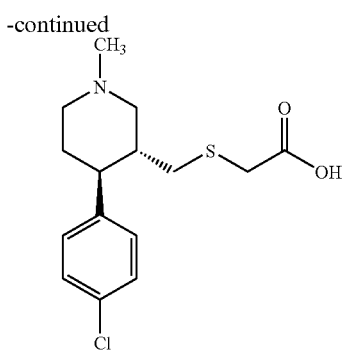

To a solution of the above methyl ester (94.0 mg, 0.287 mmol) in TF/H$_2$O (1/1, 2 mL) was added LiOH.H$_2$O (24.1 mg, 0.574 mmol) under nitrogen at room temperature. After stirring at room temperature until the reaction was complete, as judged by TLC, the mixture was neutralized with 10% aqueous HCl solution and then extracted with CH$_2$Cl$_2$ (3×25 mL). The combined extracts were dried over anhydrous sodium sulfate, filtered and concentrated under vacuum to give the product as a colorless oil (85 mg, 94%). $[\alpha]^{25}_D$ +74.1° (c 0.14, CH$_3$OH); $^1$H NMR (CD$_3$OD, 300 MHz) δ 1.98-2.08 (m, 1H), 2.12-2.26 (m, 1H), 2.33 (dd, J=9.6 and 14.1 Hz, 1H), 2.54-2.66 (m, 2H), 2.78 (td, J=3.6 and 14.0 Hz, 1H), 2.99 (s, 3H), 3.07-3.31 (m, 4 H), 3.56-3.66 (m, 1H), 3.83-3.92 (m, 1H), 7.30 (d, J=8.7 Hz, 2H), 7.35 (d, J=8.7 Hz, 2H); $^{13}$C NMR (CD$_3$OD, 75 MHz) δ 32.7, 34.2, 34.5, 39.8, 44.4, 45.3, 55.6, 58.7, 130.1, 130.5, 133.9, 141.7, 173.7; MS (EI), m/z (%) 313 (M$^+$, 3), 254 (100), 222 (47), 208 (33), 125 (36), 116 (75), 115(82), 103 (21).

Example 19

2-[(3R,4S)-4-(4-Chlorophenyl)-1-methyl-piperidin-3-ylmethylsulfanyl]-N-methyl-acetamide

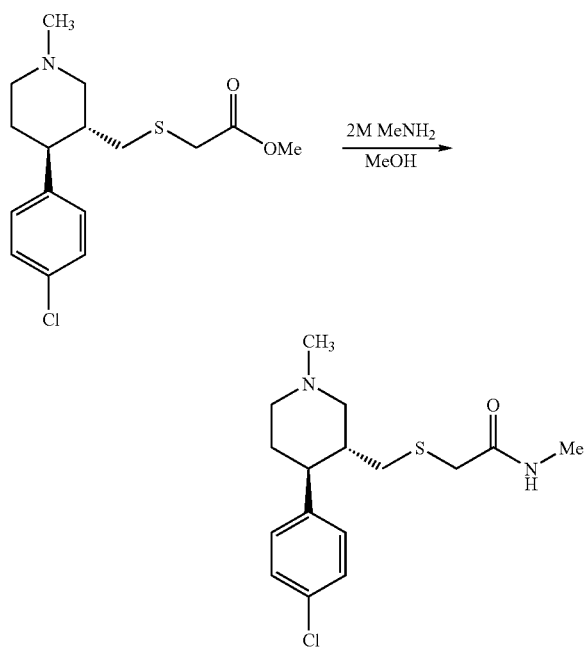

[(3R,4S)-4-(4-chlorophenyl)-1-methyl-piperidin-3-ylmethylsulfanyl]-acetic acid methyl ester (124 mg; 0.378 mmol) was dissolved in 5.0 mL of the solution of 2.0 M methylamine in MeOH. The resulting mixture was stirred at room temperature for 24 h. The reaction was monitored by TLC until the starting material almost disappeared. The solvent was then evaporated under vacuum. The crude product was purified by preparative TLC using a mixture of EtOAc/Et$_3$N (10/1) as the developing solvent to afford the product as a white solid (88.5 mg, 72%). R$_f$ [EtOAc/Et$_3$N (10/1)]=0.16. $[\alpha]^{25}_D$ +75.7° (c 0.66, CHCl$_3$); $^1$H NMR (CDCl$_3$, 300 MHz) δ 1.64-1.82 (m, 3H), 1.88-2.10 (m, 3H), 2.12-2.22 (m, 1H), 2.24-2.36 (m, 1H), 2.27 (s, 3H), 2.62 (d, J=5.1 Hz, 3H), 2.82-2.90 (m, 1H), 2.98 (q, J=13.8 and 17.4 Hz, 2H), 3.10-3.16 (m, 1H), 6.47 (br, 1H), 7.04 (d, J=8.4 Hz, 2H), 7.22 (d, J=8.7 Hz, 2H); $^{13}$C NMR (CDCl$_3$, 75 MHz) δ 26.5, 34.8, 35.4, 36.7, 41.4, 46.5, 47.0, 56.2, 60.8, 129.0 (2C overlapped), 132.4, 142.3, 168.8; MS (EI), m/z (%) 326 M$^+$, 14), 254 (100), 222 (44), 208 (64), 151 (8), 125 (22), 116 (46), 115 (45), 103 (9). Anal. (C$_{16}$H$_{23}$ClN$_2$OS)C, H, N.

Example 20

2-[(3R,4S)-4-(4-Chlorophenyl)-1-methyl-piperidin-3-ylmethanesulfinyl]-N-meth 1-acetamide

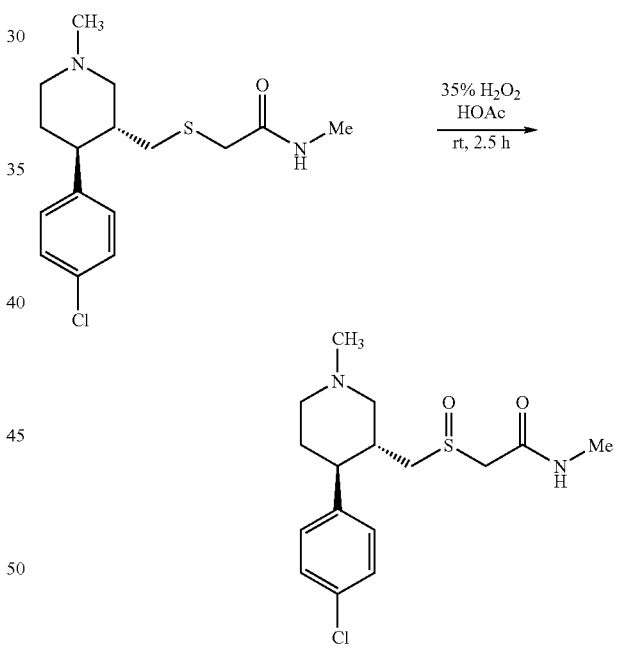

To a solution of 2-[(3R,4S)-4-(4-chlorophenyl)-1-methyl-piperidin-3-ylmethylsulfanyl]-N-methyl-acetamide (44 mg, 0.135 mmol) in acetic acid (1.5 mL) was added 14 µL of 35% H$_2$O$_2$ at room temperature. After stirring at room temperature for 2.5 h, the solvent was evaporated under vacuum. The crude product was purified by preparative TLC using a mixture of EtOAc/MeOH/Et$_3$N (8/1/1) as the developing solvent to provide the product a colorless oil (37 mg, 80%). R$_f$ [EtOAc/MeOH/Et$_3$N (8/1/1)]=0.27. $[\alpha]^{25}_D$ +77.0° (c 0.34, CHCl$_3$); $^1$H NMR (CDCl$_3$, 300 MHz) δ 1.80-1.90 (m, 2H), 1.92-2.14 (m, 2H), 2.26-2.42 (m, 2H), 2.35 (ds, 3H), 2.45-2.62 (m, 2H), 2.65 and 2.73 (both d, J=4.8 Hz, 3H), 2.94-3.04 (m, 1H), 3.10 (dd, J=14.4 and 16.8 Hz, 1H), 3.18-3.34 (m, 1H), 3.48 (dd, J=1.5 and 14.3 Hz, 1H), 6.84 (br, 1H), 7.12 (dd, J=2.4 and 8.7 Hz, 2H), 7.29 (dd, J=2.7 and 8.4 Hz, 2H); $^{13}$C NMR (CDCl$_3$, 75 MHz) δ 26.3 and 26.4 (1C), 34.4 and 34.6 (1C), 36.5 and 38.8 (1C), 46.2 (1C), 47.2 and 47.7 (1C), 53.8 and 54.0 (1C), 54.1 and 54.3 (1C), 55.8 and 55.9 (1C), 60.6 and 61.1 (1C), 129.2 (1C), 129.3 (1C), 132.8 and 132.9 (1C), 141.4 (1C), 164.4 and 164.6 (1C); MS (EI), m/z (%) 325 (M$^+$-17, 7), 270 (9), 220 (100), 125 (8), 115 (17). Anal. (C$_{16}$H$_{23}$ClN$_2$O$_2$S.0.8HCl) C, H, N.

Example 21

2-[(3R,4S)-4-(4-Chlorophenyl)-1-methyl-piperidin-3-ylmethylsulfanyl]-N,N-dimethyl-acetamide

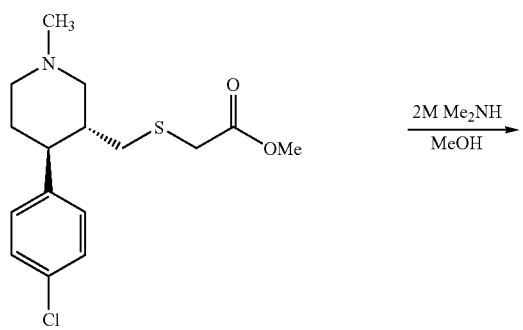

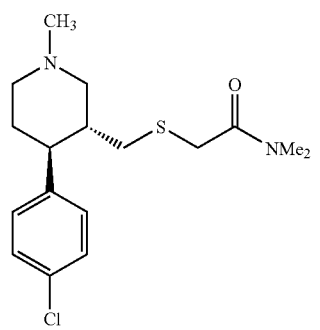

[(3R,4S)-4-(4-chlorophenyl)-1-methyl-piperidin-3-ylmethylsulfanyl]-acetic acid methyl ester (92 mg; 0.281 mmol) was dissolved in 4.0 mL of the solution of 2.0 M dimethylamine in MeOH. The resulting mixture was stirred at room temperature. The reaction was monitored by TLC until the starting material almost disappeared. The solvent was then evaporated under vacuum. The crude product was purified by preparative TLC using a mixture of EtOAc/Et$_3$N (10/1) as the developing solvent to afford the product as a colorless oil (87 mg, 91%). R$_f$ [EtOAc/Et$_3$N (10/1)]=0.28. [α]$^{25}_D$ +75.3° (c 0.38, CHCl$_3$); $^1$H NMR (CDCl$_3$, 300 MHz) δ 1.75-1.87 (m, 3H), 1.97-2.04 (m, 1H), 2.04-2.16 (m, 1H), 2.20-2.28 (m, 2H), 2.34 (s, 3H), 2.50 (dd, J=2.7 and 12.8 Hz, 1H), 2.88 (s, 3H), 2.89-2.97 (m, 1H), 2.98 (s, 3H), 3.15 (q, J=13.8 and 17.4 Hz, 2H), 3.20-3.28 (m, 1H), 7.13 (d, J=8.4 Hz, 2H), 7.26 (d, J=8.4 Hz, 2H); $^{13}$C NMR (CDCl$_3$, 75 MHz) δ 34.5, 34.6, 34.7, 35.8, 37.9, 41.4, 46.5, 47.0, 56.2, 60.7, 128.8, 129.1, 132.2, 142.5, 168.9; MS (EI), m/z (%) 340 (M$^+$, 5), 254 (100), 220 (29), 206 (33), 125 (14), 116 (51), 115 (28). Anal. (C$_{17}$H$_{25}$ClN$_2$OS.0.5H$_2$O)C, H, N.

Example 22

2-[(3R,4S)-4-(4-Chlorophenyl-1-methyl-piperidin-3-ylmethanesulfinyl]-N,N-dimethyl-acetamide

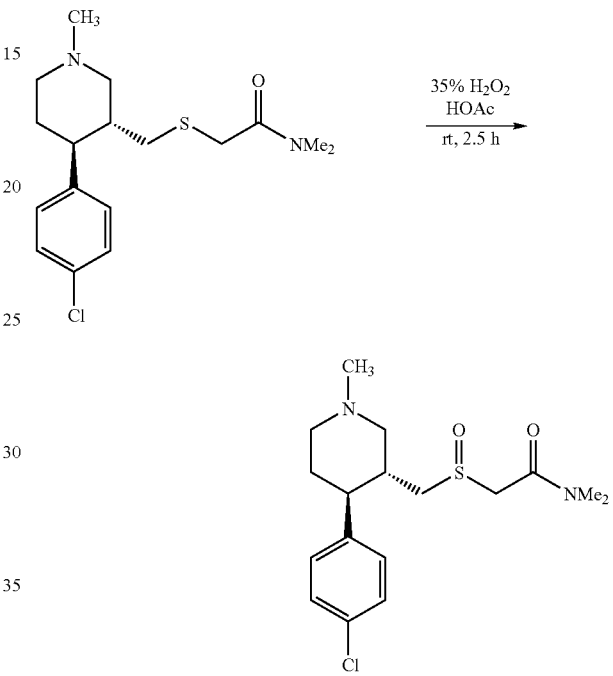

To a solution of 2-[(3R,4S)-4-(4-chlorophenyl)-1-methyl-piperidin-3-ylmethylsulfanyl]-N,N-dimethyl-acetamide (54 mg, 0.158 mmol) in acetic acid (1.5 mL) was added 15.7 μL of 35% H$_2$O$_2$ at room temperature. After stirring at room temperature for 2.5 h, the solvent was evaporated under vacuum. The crude product was purified by preparative TLC using a mixture of EtOAc/MeOH/Et$_3$N (8/1/1) as the developing solvent to provide the product a colorless oil (49 mg, 87%). R$_f$ [EtOAc/MeOH/Et$_3$N (8/1/1)]=0.34. [α]$^{25}_D$ +93.1° (c 0.48, CHCl$_3$); $^1$H NMR (CDCl$_3$, 300 MHz) δ 1.78-1.94 (m, 2H), 1.96-2.16 (m, 2H), 2.28-2.42 (m, 1H), 2.36 (ds, 3H), 2.52-2.64 (m, 2H), 2.66-2.78 (m, 1H), 2.91 (ds, 3H), 3.00 (ds, 3H), 2.96-3.04 (m, 1H), 3.27-3.42 (m, 1H), 3.58 (dd, J=3.3 and 14.0 Hz, 1H), 3.72 (dd, J=14.7 and 39.6 Hz, 1H), 7.15 (dd, J=5.7 and 8.1 Hz, 2H), 7.28 (d, J=9.0 Hz, 2H); $^{13}$C NMR (CDCl$_3$, 75 MHz) δ 34.1 and 34.6 (1C), 35.5 and 35.7 (1C), 36.4 and 38.6 (1C), 38.0 and 38.2 (1C), 46.0 and 46.1 (1C), 47.2 and 47.5 (1C), 55.6 and 55.8 k (1C), 55.9 and 56.0 (1C), 56.2 and 56.4 (1C), 60.4 and 61.0 (1C), 129.0 and 129.1 (1C), 129.2 and 129.4 (1C), 132.6 and 132.7 (1C), 141.5 and 141.7 (1C), 164.1 and 164.5 (1C); MS (EI), m/z (%) 339 (M$^+$-17, 2), 270 (10), 220 (100), 125 (8), 119 (21), 116 (12), 115 (17). Anal. (C$_{17}$H$_{25}$ClN$_2$O$_2$S.4/5H$_2$O)C, H, N.

Example 23

2-[(3R,4S-4-(4-Chlorophenyl)-1-methyl-piperidin-3-ylmethylsulfanyl]-N-isopropyl-acetamide

Example 24

2-[(3R,4S)-4-(4-Chlorophenyl)-1-methyl-piperidin-3-Ylmethanesulfinyl]-N-isopropyl-acetamide

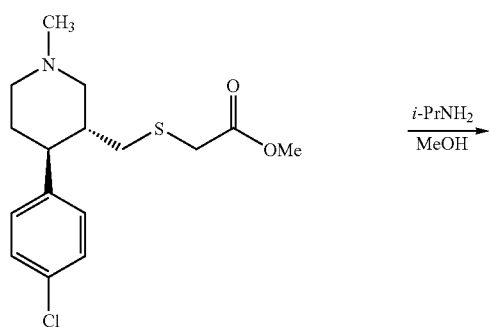

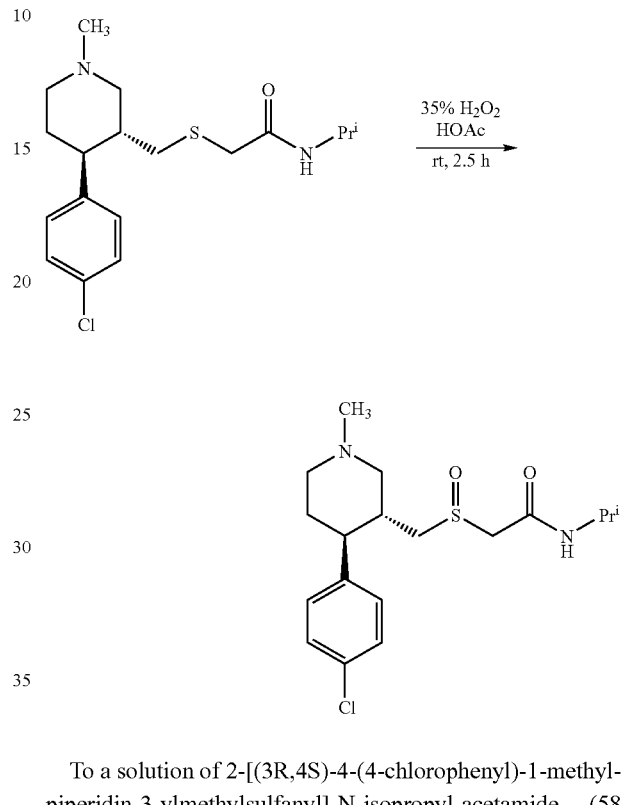

[(3R,4S)-4-(4-chlorophenyl)-1-methyl-piperidin-3-ylmethylsulfanyl]-acetic acid methyl ester (116 mg; 0.354 mmol) was dissolved in the mixture of 1.0 mL of MeOH and 2.0 mL of isopropylamine. The resulting solution was stirred at room temperature. The reaction was monitored by TLC until the starting material almost disappeared. The solvent was then evaporated under vacuum. The crude product was purified by preparative TLC using a mixture of EtOAc/Et$_3$N (10/1) as the developing solvent to afford the product as a white solid (103 mg, 82%). R$_f$ [EtOAc/Et$_3$N (10/1)]=0.40. [α]$^{25}_D$ +72.7° (c 0.55, CHCl$_3$); $^1$H NMR (CDCl$_3$, 300 MHz) δ 0.93 (d, J=6.6 Hz, 3H), 0.97 (d, J=6.6 Hz, 3H), 1.68-1.78 (m, 3H), 1.88-2.08 (m, 3H), 2.10-2.22 (m, 1H), 2.24-2.30 (m, 1H), 2.27 (s, 3H), 2.82-2.88 (m, 1H), 2.95 (q, J=16.5 and 26.3 Hz, 2H), 3.10-3.19 (m, 1H), 3.80-3.92 (m, 1H), 6.36 (d, J=7.8 Hz, 1H), 7.03 (d, J=8.4 Hz, 2H), 7.20 (d, J=8.4 Hz, 2H); $^{13}$C NMR (CDCl$_3$, 75 MHz) δ 22.6 (2C overlapped), 34.8, 35.2, 36.7, 41.1, 41.6, 46.5, 47.2, 56.2, 60.9, 128.9, 129.0, 132.5, 142.3, 167.1; MS (EI), m/z (%) 354 (M$^+$, 11), 254 (100), 222 (32), 208 (53), 125 (14), 116 (36), 115 (24). Anal. (C$_{18}$H$_{27}$ClN$_2$OS)C, H, N.

To a solution of 2-[(3R,4S)-4-(4-chlorophenyl)-1-methyl-piperidin-3-ylmethylsulfanyl]-N-isopropyl-acetamide (58 mg, 0.163 mmol) in acetic acid (2.0 mL) was added 16.2 μL of 35% H$_2$O$_2$ at room temperature. After stirring at room temperature for 2.5 h, the solvent was evaporated under vacuum. The crude product was purified by preparative TLC using a mixture of EtOAc/MeOH/Et$_3$N (8/1/1) as the developing solvent to provide the product a colorless oil (52 mg, 86%). R$_f$ [EtOAc/MeOH/Et$_3$N (8/1/1)]=0.57. [α]$^{25}_D$ +76.8° (c 0.50, CHCl$_3$); $^1$H NMR (CDCl$_3$, 300 MHz) δ 0.82 and 0.94 (d, J=6.6 Hz, 3H), 1.01 and 1.04 (d, J=6.6 Hz, 3H), 1.72-1.84 (m, 2H), 1.84-2.05 (m, 2H), 2.18-2.36 (m, 2H), 2.28 (ds, 3H), 2.38-2.58 (m, 2H), 2.84-2.94 (m, 1H), 2.96 (dd, J=2.1 and 11.0 Hz, 1H), 3.14-3.28 (m, 1H), 3.41 (dd, J=7.2 and 14.3 Hz, 1H), 3.78-3.98 (m, 1H), 6.68 (dd, J=7.5 Hz, 1H), 7.06 (dd, J=3.3 and 8.4 Hz, 2H), 7.22 (dd, J=3.6 and 8.4 Hz, 2H); $^{13}$C NMR (CDCl$_3$, 75 MHz) δ 22.4 and 22.5 (1C), 22.6 (2C overlapped), 34.3 and 34.6 (1C), 36.5 and 38.6 (1C), 41.9 and 42.0 (1C), 46.1 and 46.2 (1C), 47.3 and 47.7 (1C), 53.9 and 54.1 (1C), 55.7 and 55.8 (1C), 60.5 and 61.1 (1C), 129.1 (1C), 129.2 and 129.3 (1C), 132.8 and 132.9 (1C), 141.3 (1C), 162.8 and 162.9 (1C); MS (EI), m/z (%) 353 (M$^+$-17, 3), 270 (9), 220 (100), 186 (12), 133 (13), 125 (8), 116 (12), 115 (17). Anal. (C$_{18}$H$_{27}$ClN$_2$O$_2$S.0.9HCl) C, H, N.

Example 25

2-[(3R,4S)-4-(4-Chlorophenyl)-1-methyl-piperidin-3-ylmethylsulfanyl]-1-piperidin-1-yl-ethanone

Example 26

2-[(3R,4S)-4-(4-Chlorophenyl)-1-methyl-piperidin-3-ylmethanesulfinyl]-1-piperidin-1-yl-ethanone

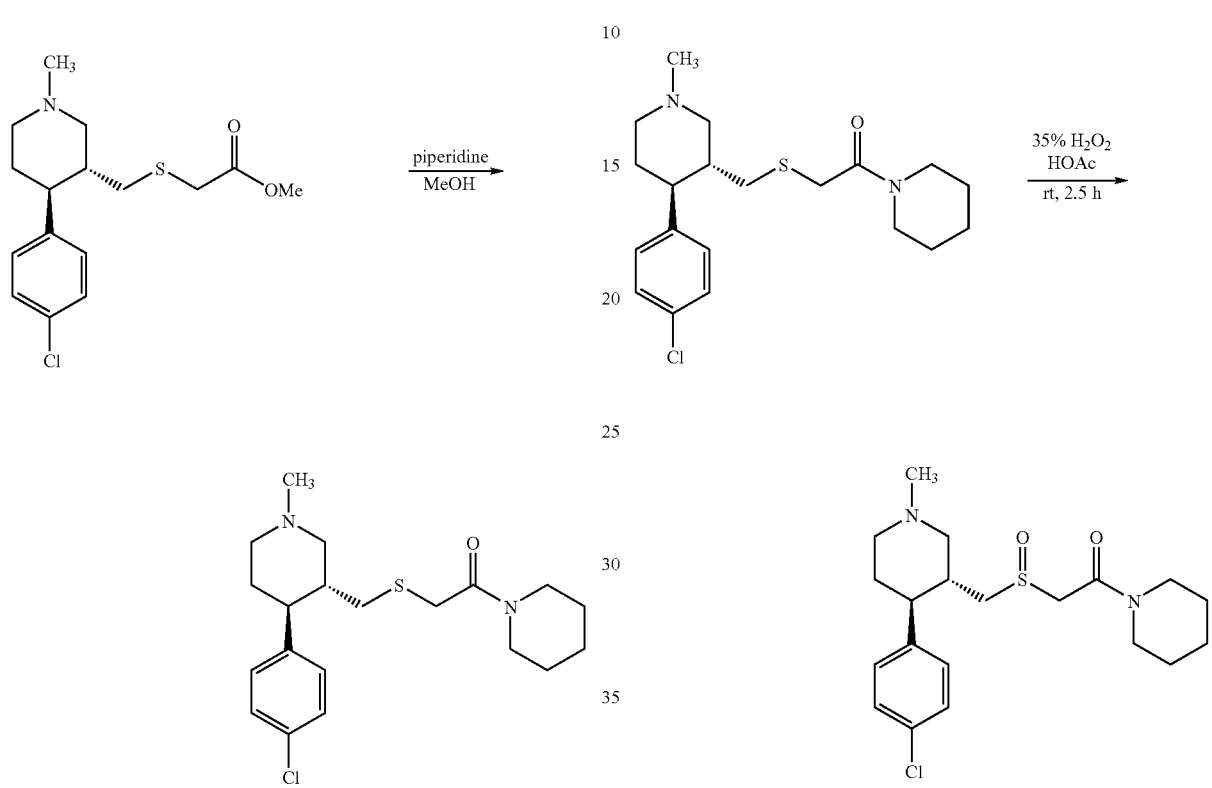

[(3R,4S)-4-(4-chlorophenyl)-1-methyl-piperidin-3-ylmethylsulfanyl]-acetic acid methyl ester (117 mg; 0.357 mmol) was dissolved in the mixture of 1.0 mL of MeOH and 2.0 mL of piperidine. The resulting solution was stirred at room temperature. The reaction was monitored by TLC until the starting material almost disappeared. The solvent was then evaporated under vacuum. The crude product was purified by preparative TLC using a mixture of EtOAc/Et$_3$N (10/1) as the developing solvent to afford the product as a pale yellow oil (125 mg, 92%). R$_f$[EtOAc/Et$_3$N (10/1)]=0.38. [α]$^{25}_D$ +72.4° (c 0.40, CHCl$_3$); $^1$H NMR (CDCl$_3$, 300 MHz) δ 1.38-1.48 (m, 2H), 1.52-1.66 (m, 4H), 1.72-1.86 (m, 3H), 1.96-2.05 (m, 1H), 2.06-2.16 (m, 1H), 2.19-2.26 (m, 2H), 2.34 (s, 3H), 2.48 (dd, J=2.7 and 12.6 Hz, 1H), 2.91-2.96 (m, 1H), 3.17 (q, J=13.8 and 17.1 Hz, 2H), 3.21-3.25 (m, 1H), 3.32 (dd, J=5.4 and 5.6 Hz, 2H), 3.45 (dd, J=4.8 and 5.5 Hz, 2H), 7.14 (d, J=8.7 Hz, 2H), 7.26 (d, J=8.4 Hz, 2H); $^{13}$C NMR (CDCl$_3$, 75 MHz) δ 24.3, 25.5, 26.3, 34.5, 34.6, 34.7, 41.1, 42.9, 46.4, 47.0, 47.4, 56.1, 60.7, 128.7, 129.0, 132.1, 142.4, 167.0; MS (EI), m/z (%) 380 (M$^+$, 2), 254 (100), 220 (23), 206 (24), 127 (20), 125 (12), 116 (53), 115 (22). Anal. (C$_{20}$H$_{29}$ClN$_2$OS.0.5H$_2$O) C, H, N.

To a solution of 2-[(3R,4S)-4-(4-chlorophenyl)-1-methyl-piperidin-3-ylmethylsulfanyl]-1-piperidin-1-yl-ethanone (56 mg, 0.147 mmol) in acetic acid (2.0 mL) was added 14.5 μL of 35% H$_2$O$_2$ at room temperature. After stirring at room temperature for 2.5 h, the solvent was evaporated under vacuum. The crude product was purified by preparative TLC using a mixture of EtOAc/MeOH/Et$_3$N (84/8/8) as the developing solvent to provide the product a colorless oil (44 mg, 75%). R$_f$[EtOAc/MeOH/Et$_3$N (8/1/1)]=0.46. [α]$^{25}_D$ +79.0° (c 0.39, CHCl$_3$); $^1$H NMR (CDCl$_3$, 300 MHz) δ 1.42-1.54 (m, 4H), 1.54-1.68 (m, 2H), 1.74-1.92 (m, 2H), 1.94-2.16 (m, 2H), 2.36 (ds, 3H), 2.26-2.44 (m, 1H), 2.46-2.76 (m, 3H), 2.96-3.04 (m, 1H), 3.26-3.40 (m, 3H), 3.42-3.53 (m, 2H), 3.60 (dd, J=1.5 and 12.9 Hz, 1H), 3.69 (dd, J=14.1 and 34.7 Hz, 1H), 7.14 (dd, J=5.4 and 8.4 Hz, 2H), 7.28 (dd, J=2.7 and 8.4 Hz, 2H); $^{13}$C NMR (CDCl$_3$, 75 MHz) δ 24.3 (1C), 25.5 (1C), 26.6 and 26.7 (1C), 34.3 and 34.8 (1C), 36.4 and 38.6 (1C), 43.1 and 43.2 (1C), 46.1 and 46.2 (1C), 47.2 and 47.5 (1C), 47.7 and 47.9 (1C), 55.7 and 55.8 (1C), 55.9 and 56.1 (1C), 56.2 and 56.9 (1C), 60.4 and 61.2 (1C), 129.1 and 129.2 (1C), 129.3 and 129.5 (1C), 132.6 and 132.7 (1C), 141.6 and 141.8 (1C), 162.2 and 162.6 (1C); MS (EI), m/z (%) 379 (M$^+$-17, 1), 270 (12), 220 (100), 186 (6), 159 (13), 126 (12), 116 (10), 115 (14). Anal. (C$_{20}$H$_{29}$ClN$_2$O$_2$S.0.6HCl) C, H, N.

Example 27

(3R,4S)-4-(4-Chlorophenyl)-1-methyl-3-(3-methyl-1,24-oxadiazol-5-ylmethylsulfanylmethyl)-piperidine

Example 28

(3R,4S)-4-(4-Chlorophenyl)-1-methyl-3-(3-methyl-1,2,4-oxadiazol-5-ylmethanesulfinylmethyl)-piperidine

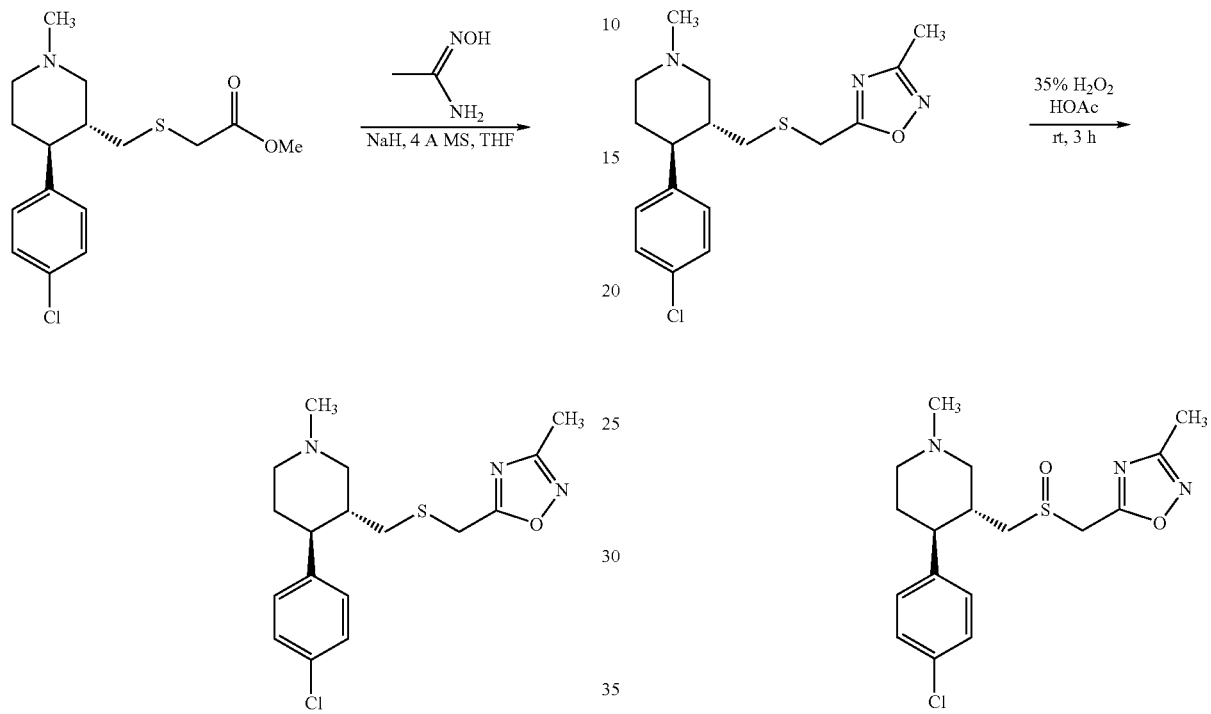

To a solution of acetamide oxime (67.8 mg, 0.915 mmol) in anhydrous THF (8.0 mL) was added NaH (38.5 mg, 57-63% suspension in oil, 0.915 mmol) at room temperature. The resulting mixture was stirred at reflux for 2.5 h and then cooled down to room temperature. To the reaction mixture was added 4 Å molecular sieves (700 mg), followed by the solution of [(3R,4S)-4-(4-chlorophenyl)-1-methyl-piperidin-3-ylmethylsulfanyl]-acetic acid methyl ester (150 mg, 0.4575 mmol) in 2.0 mL of THF. The resulting mixture was stirred at reflux for 16 h and then cooled down to room temperature. The reaction mixture was filtered and rinsed with THF. The solvent of the combined organics was then evaporated under vacuum. The crude product was purified by column chromatography on silica gel with EtOAc/Et$_3$N (98:2) as the eluent to yield the product as a colorless oil (127 mg, 79%). R$_f$ [EtOAc/Et$_3$N (10/1)]=0.54. [α]$^{25}_D$ +106.0° (c 0.52, CHCl$_3$); $^1$H NMR (CDCl$_3$, 300 MHz) δ 1.65-1.80 (m, 3H), 1.87-2.04 (m, 2H), 2.07-2.22 (m, 2H), 2.24 (s, 3H), 2.25 (s, 3H), 2.46 (dd, J=2.7 and 12.6 Hz, 1H), 2.83-2.89 (m, 1H), 3.09-3.16 (m, 1H), 3.56 (q, J=15.3 and 23.4 Hz, 2H), 7.01 (d, J=8.7 Hz, 2H), 7.17 (d, J=8.1 Hz, 2H); $^{13}$C NMR (CDCl$_3$, 75 MHz) δ 11.6, 26.0, 34.5 (2C overlapped), 41.0, 46.4, 46.9, 56.1, 60.7, 128.8, 128.9, 132.2, 142.1, 167.3, 176.3; MS (EI), m/z (%) 351 (M$^+$, 9), 254 (100), 220 (69), 206 (29), 151 (10), 127 (18), 125 (31), 116 (64), 115 (60), 103 (14). Anal. (C$_{17}$H$_{22}$ClN$_3$OS.1/5H$_2$O)C, H, N.

To a solution of (3R,4S)-4-(4-chlorophenyl)-1-methyl-3-(3-methyl-1,2,4-oxadiazol-5-ylmethylsulfanylmethyl)-piperidine (58 mg, 0.165 mmol) in acetic acid (2.0 mL) was added 16.3 µL of 35% H$_2$O$_2$ at room temperature. After stirring at room temperature for 3 h, the solvent was evaporated under vacuum. The crude product was purified by preparative TLC using a mixture of EtOAc/Et$_3$N (10/1) as the developing solvent to provide the product a colorless oil (35.4 mg, 66%) and 7 mg of the starting material was recovered. R$_f$ [EtOAc/Et$_3$N (10/1)]=0.30. [α]$^{25}_D$ +81.4° (c 0.42, CHCl$_3$); $^1$H NMR (CDCl$_3$, 300 MHz) δ 1.82-1.94 (m, 2H), 1.96-2.16 (m, 2H), 2.26-2.44 (m, 1H), 2.35 (s, 3H), 2.36 (s, 3H), 2.46-2.54 (m, 1H), 2.58-2.76 (m, 2H), 2.94-3.06 (m, 1H), 3.24-3.36 (m, 1H), 3.99 (dd, J=14.1 and 24.8 Hz, 1H), 4.12 (dd, J=2.7 and 14.0 Hz, 1H), 7.10 (dd, J=5.7 and 8.4 Hz, 2H), 7.27 (dd, J=3.9 and 8.4 Hz, 2H); $^{13}$C NMR (CDCl$_3$, 75 MHz) δ 11.6 (1C), 34.2 and 34.7 (1C), 37.2 and 39.4 (1C), 46.3 (1C), 47.0 and 47.7 (1C), 48.2 and 48.3 (1C), 55.4 and 55.5 (1C), 55.8 and 55.9 (1C), 60.5 and 61.2 (1C), 129.1 and 129.2 (1C), 129.3 and 129.5 (1C), 132.8 and 132.9 (1C), 141.3 and 141.4 (1C), 167.8 and 167.9 (1C), 169.9 (1C); MS (EI), m/z (%) 350 (M$^+$-17, 3), 270 (10), 220 (100), 129 (13), 128 (14), 127 (12), 125 (21), 116 (29), 115 (45), 103 (11). Anal. (C$_{17}$H$_{22}$ClN$_3$O$_2$S.H$_2$O)C, H, N.

Example 29

[(3R,4S)-4-(4-Chlorophenyl)-piperidin-3-ylmethyl-sulfanyl]-acetic Acid Methyl Ester

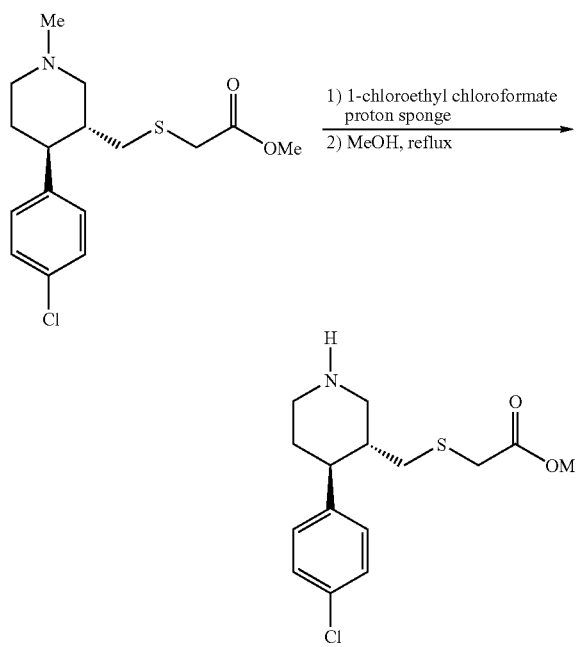

To a solution of [(3R,4S)-4-(4-chlorophenyl)-1-methyl-piperidin-3-ylmethylsulfanyl]-acetic acid methyl ester (342 mg, 1.04 mmol) in anhydrous $CH_2Cl_2$ (10 mL) were added 1,8-bisdimthylaminonaphthalene (proton sponge, 122.6 mg, 0.57 mmol) and α-chloroethyl chloroformate (0.85 mL, 1.12 g, 7.83 mmol) at room temperature. The resulting mixture was stirred at reflux for 2.5 h and then cooled down to room temperature. To the reaction mixture was added 1 M anhydrous hydrogen chloride solution in ether (10 mL). The suspension was filtered through a silica gel plug, and the residue was rinsed with $CH_2Cl_2$ (2×10 mL). The filtrate was concentrated and mixed with 15 mL of MeOH. The resulting mixture was stirred at reflux for 1 h and then evaporated under vacuum. The residue was mixed with a 0.5 M solution of KOH (4 mL) and extracted with EtOAc (3×25 mL). The combined organic extract was washed with brine, dried over $Na_2SO_4$, concentrated and purified by column chromatography on silica gel with $EtOAc/Et_3N$ (98:2) to $EtOAc/MeOH/Et_3N$ (90:5:5) as the eluent to yield the product as a colorless oil (261 mg, 80%). $R_f$ [$EtOAc/MeOH/Et_3N$ (8:1:1)]=0.37. $[\alpha]^{25}_D$ +76.4° (c 0.34, $CHCl_3$); $^1H$ NMR ($CDCl_3$, 300 MHz) δ 1.56-1.72 (m, 2H), 1.78-1.92 (m, 1H), 2.08 (dd, J=9.3 and 12.9 Hz, 1H), 2.24-2.43 (m, 3H), 2.60 (dt, J=3.0 and 10.6 Hz, 1H), 2.98 (dd, J=14.7 and 23.9 Hz, 2H), 3.02-3.12 (m, 1H), 3.39 (dd, J=3.6 and 12.0 Hz, 1H)$_2$ 3.53 (s, 3H), 7.05 (d, J=8.7 Hz, 2H), 7.20 (d, J=8.7 Hz, 2H); $^{13}C$ NMR ($CDCl_3$, 75 MHz) δ 4.0, 34.9, 35.5, 42.0, 47.0, 48.1, 51.5, 52.3, 128.8, 128.9, 132.1, 142.7, 170.7; MS (EI), m/z (%) 313 (M$^+$, 13), 242 (37), 240 (100), 208 (55), 194 (53), 151 (12), 129 (18), 128 (21), 125 (36), 116 (35), 115 (60), 103 (22). Anal. ($C_{15}H_{20}ClNO_2S.2/5H_2O$)C, H, N.

Example 30

2-[(3R,4S)-4-(4-Chlorophenyl)-piperidin-3-ylmethylsulfanyl]-acetamide

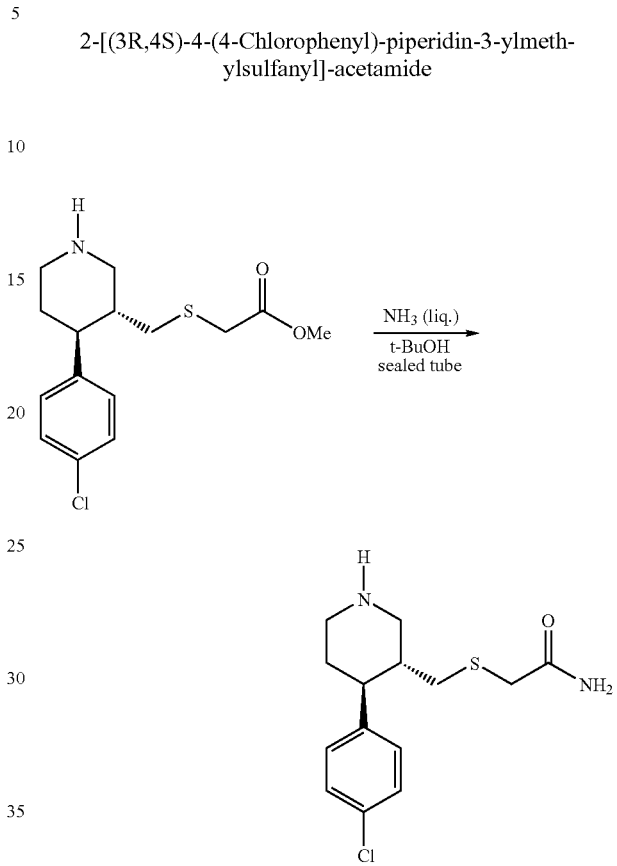

To a solution of [(3R,4S)-4-(4-chlorophenyl)-piperidin-3-ylmethylsulfanyl]-acetic acid methyl ester (152.5 mg, 0.486 mmol) in t-BuOH (3 mL) in a tube that was cooled with dry ice-acetone bath was introduced excess ammonium gas. Then the tube was sealed and the reaction mixture was stirred at room temperature for 72 h. The solvent was evaporated under vacuum. The crude product was purified by column chromatography on a silica gel using a mixture of $EtOAc/MeOH/Et_3N$ (6/2/2) as the eluent to give the product as a pale yellow oil, which was further purified by HPLC to afford the desired product as a colorless oil (130 mg, 90%). $R_f$[$EtOAc/MeOH/Et_3N$ (6/2/2)]=0.24. $[\alpha]^{25}_D$ +104.8° (c 0.11, $CHCl_3$); $^1H$ NMR ($CD_3OD$, 300 MHz) δ 1.84-2.04 (m, 2H), 2.24-2.40 (m, 2H), 2.48-2.60 (m, 1H), 2.70 (td, J=3.9 and 18.3 Hz, 1H), 2.90 (t, J=11.7 Hz, 1H), 3.00-3.14 (m, 3H), 3.44-3.54 (m, 1H), 3.76-3.84 (m, 1H), 7.24 (dd, J=1.2 and 8.7 Hz, 2H), 7.37 (dd, J=1.2 and 8.7 Hz, 2H); $^{13}C$ NMR ($CD_3OD$, 75 MHz) δ 32.2, 34.8, 36.3, 39.7, 45.6, 46.4, 48.9, 130.2, 130.3, 134.2, 142.0, 174.9; MS (EI), m/z (%) 298 (M$^+$, 7), 240 (74), 208 (85), 194 (100), 151 (18), 128 (26), 125 (48), 116 (41), 115 (68), 103 (22), 102 (46). HPLC conditions are as follows: Column: Waters μ Bondapak $C_{18}$300×7.8 mm; Flow rate: 2.8 mL/min; Detection at 280 nm; Gradient from 10% acetonitrile in water (0.05% $CF_3COOH$) to 40% acetonitrile in water (0.05% CF$_3$COOH) in 30 min and stop running in 60 min; HPLC Purity: 98%; $t_R$=26.63 min.

Example 31

2-[(3R,4S)-4-(4-Chlorophenyl)-piperidin-3-yl-methanesulfinyl]-acetamide

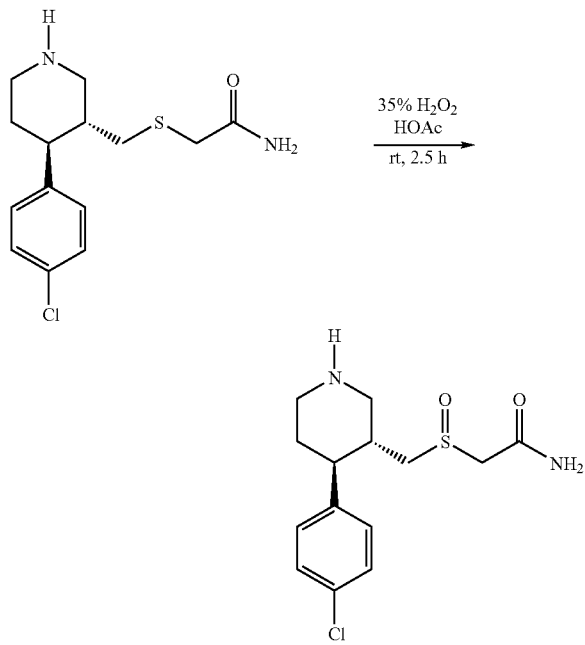

To a solution of 2-[(3R,4S)-4-(4-chlorophenyl)-piperidin-3-ylmethylsulfanyl]-acetamide (68 mg, 0.228 mmol) in acetic acid (2.0 mL) was added 22.6 μL of 35% H$_2$O$_2$ at room temperature. After stirring at room temperature for 2.5 h, the solvent was evaporated under vacuum. The crude product was purified by preparative TLC using a mixture of EtOAc/MeOH/Et$_3$N/NH$_3$.H$_2$O (60/19/19/2) as the developing solvent to afford the product as a colorless oil, which was further purified by HPLC to give the desired product as a white solid (52 mg, 73%). R$_f$[EtOAc/MeOH/Et$_3$N/NH$_3$.H$_2$O (60/19/19/2)]=0.27. [α]$^{25}_D$ +72.2° (c 0.21, CHCl$_3$); $^1$H NMR (CD$_3$OD, 300 MHz) δ 1.84-2.12 (m, 2H), 2.58-2.92 (m, 4H), 2.94-3.22 (m, 2H), 3.46-3.70 (m, 3H), 3.74-3.84 (m, 1H), 7.27 (dd, J=2.7 and 8.4 Hz, 2H), 7.37 (dd, J=2.7 and 8.4 Hz, 2H); $^{13}$C NMR (CD$_3$OD, 75 MHz) δ 32.1 and 32.4 (1C), 35.6 and 37.4 (1C), 45.3 and 45.5 (1C), 46.0 and 46.8 (1C), 48.4 and 49.3 (1C), 54.4 and 54.7 (1C), 58.1 and 58.6 (1C), 130.5 and 130.6 (1C), 130.6 and 130.7 (1C), 134.5 and 134.6 (1C), 141.3 and 141.5 (1C), 168.5 and 168.6 (1C); MS (EI), m/z (%) 297 (M$^+$-17, 4), 256 (7), 206 (100), 125 (16), 116 (15), 115 (25). HPLC conditions are as follows: Column: Waters μ Bondapak C$_{18}$ 300×7.8 mm; Flow rate: 2.8 mL/min; Detection at 280 nm; Gradient from 10% acetonitrile in water (0.05% CF$_3$COOH) to 40% acetonitrile in water (0.05% CF$_3$COOH) in 30 min and stop running in 60 min; HPLC Purity: 97%; $t_R$=21.73 min.

Example 32

Synaptosomal Uptake of [$^3$H]Dopamine, [$^3$H]5-Hydroxytryptamine, and [$^3$H]Norepinephrine Compounds were tested as the free base. The effect of candidate compounds in antagonizing biogenic amine high-affinity uptake was determined as previously described by Wang et al. Wang, S.; Sakamuri, S.; Enyedy, I. J.; Kozikowski, A. P.; Deschaux, O.; Bandyopadhyay, B. C.; Tella, S. R.; Zaman, W. A.; Johnson, K. M. J. Med. Chem. 2000, 43, 351-360. Striatum, midbrain, and parietal/occipital cortex were dissected and used as a source of rat DAT, SERT, and NET, respectively. These brain regions were homogenized with a Teflon-glass pestle in ice-cold 0.32 M sucrose and centrifuged for 10 min at 1000 g. The supernatant was centrifuged at 17500 g for 20 min. This P$_2$ synaptosomal pellet was resuspended in 30 volumes of ice-cold modified KRH buffer consisting of (in mM) NaCl (125), KCl (4.8), MgSO$_4$ (1.2), CaCl$_2$ (1.3), KH$_2$PO$_4$ (1.2), glucose (5.6), nialamide (0.01), and HEPES (25) (pH 7.4). An aliquot of the synaptosomal suspension was preincubated with the buffer and drug for 30 min at 4° C. and then for 15 min at 37° C. before uptake was initiated by the addition of [$^3$H]biogenic amine (~5 nM for [$^3$H]DA and [$^3$H]5-HT, 9 nM for [$^3$H]NE, final concentration). After 5 min, uptake was terminated by adding 5 mL of cold buffer containing glucosamine as a substitute for NaCl and then finally by rapid vacuum filtration over GF/C glass-fiber filters, followed by washing with two 5 mL volumes of ice-cold, sodium-free buffer. The bound and free [$^3$H]biogenic amines were separated by rapid vacuum filtration over Whatman GF/C filters, using a Brandel M24R cell harvester, followed by two washes with 5 mL of cold buffer. Radioactivity on the filters was then extracted by allowing the filters to sit overnight with 5 mL of scintillation fluid. The vials were vortexed and counted. Specific uptake of [$^3$H]DA was defined as that which is sensitive to inhibition by 30 μM cocaine. 10 μM Fluoxetine and 3 μM desipramine, respectively, were used to define the specific uptake of [$^3$H] 5-HT and [$^3$H]NE. In each instance, it was virtually identical to that calculated by subtracting the mean of identical tubes incubated at 0° C. IC$_{50}$ values were determined using the computer program LIGAND. The Cheng-Prusoff equation for classic, competitive inhibition was used for calculating K$_i$ from IC$_{50}$ values in uptake experiments. The K$_m$ values used were 67 nM for [$^3$H]DA, 53 nM for [$^3$H]5-HT, and 54 nM for [$^3$H]NE. Even though uptake is a non-equilibrium process, K$_i$ determinations are thought to be appropriate estimates of affinity between these compounds and the biogenic amine transporters because it is likely that the relatively long (45 min) period of incubation of the drug before addition of the [$^3$H] amine is adequate time for equilibrium between the test compound the biogenic amine transporter to occur.

Figure 2:
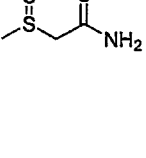
FIG. 2 depicts tabulated data for the inhibition of reuptake at monoamine transporters for various compounds.
Figure 2:
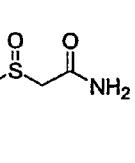
Figure 2:
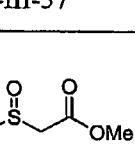
Figure 2:
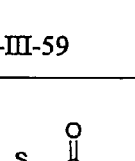
Figure 3:
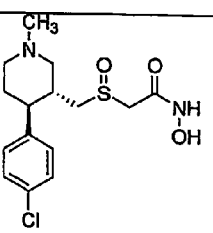
FIG. 3 depicts tabulated data for the inhibition of reuptake at monoamine transporters for various compounds.
Figure 3:
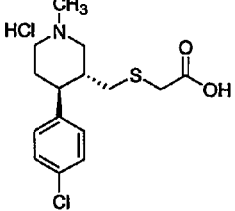
Figure 3:
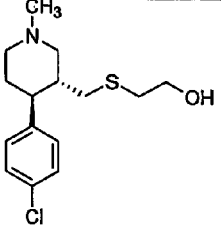
Figure 3:
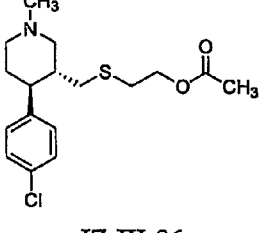
Figure 4:
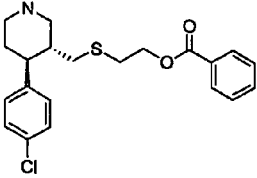
FIG. 4 depicts tabulated data for the inhibition of reuptake at monoamine transporters for various compounds.
Figure 4:
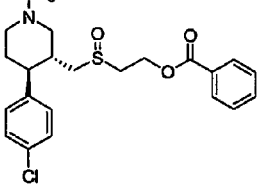
Figure 4:
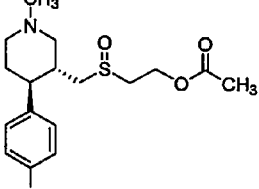
Figure 4:
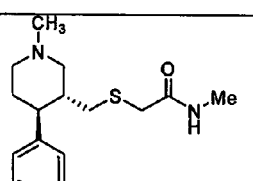
Figure 5:
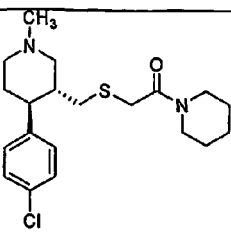
FIG. 5 depicts tabulated data for the inhibition of reuptake at monoamine transporters for various compounds.
Figure 5:
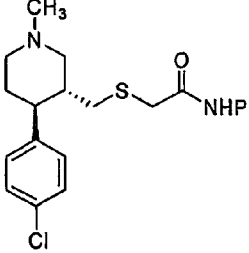
Figure 5:
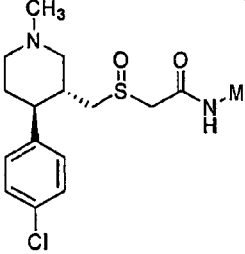
Figure 5:
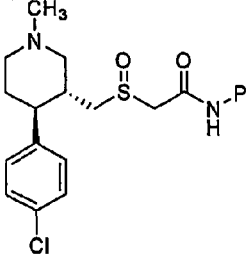
Figure 6:
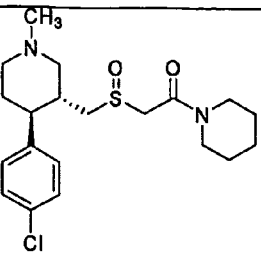
FIG. 6 depicts tabulated data for the inhibition of reuptake at monoamine transporters for various compounds.
Figure 6:
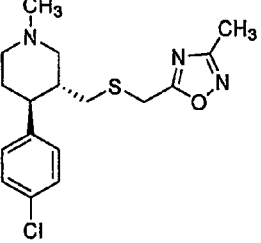
Figure 6:
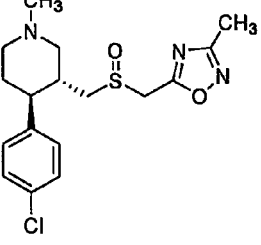
Figure 6:
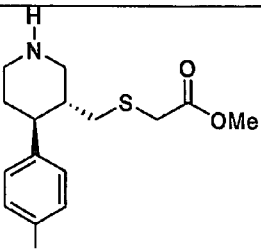
Figure 8:
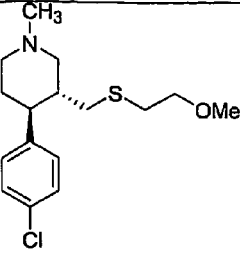
FIG. 8 depicts tabulated data for the inhibition of reuptake at monoamine transporters for various compounds.
Figure 8:
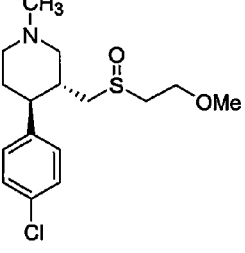
Figure 8:
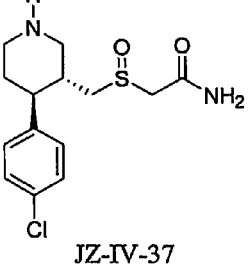

The results of the tests described above are displayed in FIGS. 1-10. The K$_i$ values are mean±SEM from two to four independent experiments, each consisting of six drug concentrations (in triplicate) that were selected on the basis of preliminary screening experiments to bracket the approximate IC$_{50}$ value. The ClogP value was calculated using software available on the internet. See <http://www.daylight.com/daycgi/clogp> and <http://esc.syrres.com/interkow/kowdemo.htm>.

Incorporation by Reference

All of the patents and publications cited herein are hereby incorporated by reference.

EQUIVALENTS

Those skilled in the art will recognize, or be able to ascertain using no more than routine experimentation, many equivalents to the specific embodiments of the invention

We claim:

1. A compound represented by formula I:

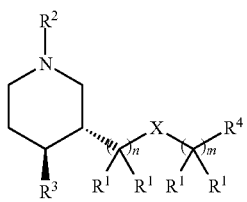

I wherein
$R^1$ represents independently for each occurrence H or alkyl;
$R^2$ is H, alkyl, aryl, aralkyl, or —C(O)$R^5$;
$R^3$ is aryl optionally substituted, heteroaryl, or aralkyl;
$R^4$ is C(O)N($R^6$)$_2$;
$R^5$ is alkyl, aryl, heteroaryl, or aralkyl;
$R^6$ represents independently for each occurrence hydrogen, alkyl, aryl, or aralkyl, wherein any two instances of $R^6$ may be covalently attached to form a ring;
X is S, —S(O)—, or —S(O$_2$)—;
n is 1, 2, 3, or 4; and
m is 1, 2, 3, or 4.

2. A compound represented by formula II:

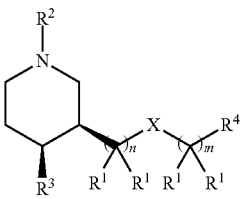

II wherein
$R^1$ represents independently for each occurrence H or alkyl;
$R^2$ is H, alkyl, aryl, aralkyl, or —C(O)$R^5$;
$R^3$ is aryl optionally substituted, heteroaryl, or aralkyl;
$R^4$ is C(O)N($R^6$)$_2$;
$R^5$ is alkyl, aryl, heteroaryl, or aralkyl;
$R^6$ represents independently for each occurrence hydrogen, alkyl, aryl, or aralkyl, wherein any two instances of $R^6$ may be covalently attached to form a ring;
X is S, —S(O)—, or —S(O$_2$)—;
n is 1, 2, 3, or 4; and
m is 1, 2, 3, or 4.

3. A compound represented by formula III:

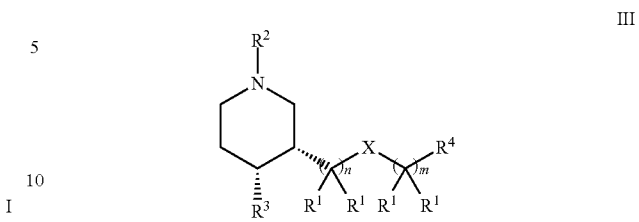

III wherein
$R^1$ represents independently for each occurrence H or alkyl;
$R^2$ is H, alkyl, aryl, aralkyl, or —C(O)$R^5$;
$R^3$ is aryl optionally substituted, heteroaryl, or aralkyl;
$R^4$ is C(O)N($R^6$)$_2$;
$R^5$ is alkyl, aryl, heteroaryl, or aralkyl;
$R^6$ represents independently for each occurrence hydrogen, alkyl, aryl, or aralkyl, wherein any two instances of $R^6$ may be covalently attached to form a ring;
X is S, —S(O)—, or —S(O$_2$)—;
n is 1, 2, 3, or 4; and
m is 1, 2, 3, or 4.

4. A compound represented by formula IV:

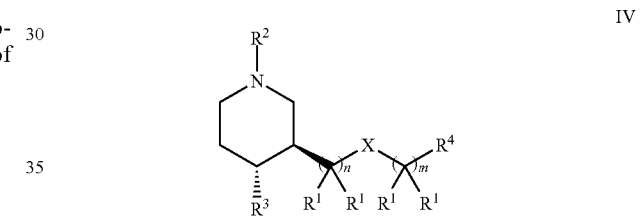

IV wherein
$R^1$ represents independently for each occurrence H or alkyl;
$R^2$ is H, alkyl, aryl, aralkyl, or —C(O)$R^5$;
$R^3$ is aryl optionally substituted, heteroaryl, or aralkyl;
$R^4$ is C(O)N($R^6$)$_2$;
$R^5$ is alkyl, aryl, heteroaryl, or aralkyl;
$R^6$ represents independently for each occurrence hydrogen, alkyl, aryl, or aralkyl, wherein any two instances of $R^6$ may be covalently attached to form a ring;
X is S, —S(O)—, or —S(O$_2$)—;
n is 1, 2, 3, or 4; and
m is 1, 2, 3, or 4.

5. The compound of claim 2, wherein X is S or —S(O)—.
6. The compound of claim 2, wherein $R^2$ is methyl, ethyl or propyl.
7. The compound of claim 2, wherein $R^2$ is methyl.
8. The compound of claim 2, wherein $R^3$ is optionally substituted phenyl.
9. The compound of claim 8, wherein $R^3$ is halophenyl.
10. The compound of claim 8, wherein $R^3$ is 3-chlorophenyl.
11. The compound of claim 2, wherein $R^6$ represents independently for each occurrence hydrogen or alkyl.
12. The compound of claim 2, wherein X is S, n is 1, m is 1, $R^1$ is hydrogen, $R^2$ is methyl, and $R^3$ is 3-chlorophenyl.
13. The compound of claim 2, wherein X is S, n is 1, m is 1, $R^1$ is hydrogen, $R^2$ is methyl, $R^3$ is 3-chlorophenyl, and $R^4$ is C(O)N(H)iPr.

14. The compound of claim 3, wherein X is S or —S(O)—.

15. The compound of claim 3, wherein $R^2$ is methyl, ethyl or propyl.

16. The compound of claim 3, wherein $R^2$ is methyl.

17. The compound of claim 3, wherein $R^3$ is optionally substituted phenyl.

18. The compound of claim 17, wherein $R^3$ is halophenyl.

19. The compound of claim 17, wherein $R^3$ is 3-chlorophenyl.

20. The compound of claim 3, wherein $R^6$ represents independently for each occurrence hydrogen or alkyl.

21. The compound of claim 3, wherein X is S, n is 1, m is 1, $R^1$ is hydrogen, $R^2$ is methyl, and $R^3$ is 3-chlorophenyl.

22. The compound of claim 3, wherein X is S, n is 1, m is 1, $R^1$ is hydrogen, $R^2$ is methyl, $R^3$ is 3-chlorophenyl, and $R^4$ is C(O)N(H)iPr.

23. The compound of claim 4, wherein X is S or —S(O)—.

24. The compound of claim 4, wherein $R^2$ is methyl, ethyl or propyl.

25. The compound of claim 4, wherein $R^2$ is methyl.

26. The compound of claim 4, wherein $R^3$ is optionally substituted phenyl.

27. The compound of claim 26, wherein $R^3$ is halophenyl.

28. The compound of claim 26, wherein $R^3$ is 3-chlorophenyl.

29. The compound of claim 4, wherein $R^6$ represents independently for each occurrence hydrogen or alkyl.

30. The compound of claim 4, wherein X is S, n is 1, m is 1, $R^1$ is hydrogen, $R^2$ is methyl, and $R^3$ is 3-chlorophenyl.

31. The compound of claim 4, wherein X is S, n is 1, m is 1, $R^1$ is hydrogen, $R^2$ is methyl, $R^3$ is 3-chlorophenyl, and $R^4$ is C(O)N(H)iPr.

32. The compound of claim 1, wherein X is S or —S(O)—.

33. The compound of claim 1, wherein $R^2$ is methyl, ethyl or propyl.

34. The compound of claim 1, wherein $R^2$ is methyl.

35. The compound of claim 1, wherein $R^3$ is optionally substituted phenyl.

36. The compound of claim 35, wherein $R^3$ is halophenyl.

37. The compound of claim 35, wherein $R^3$ is 3-chlorophenyl.

38. The compound of claim 1, wherein $R^6$ represents independently for each occurrence hydrogen or alkyl.

39. The compound of claim 1, wherein X is S, n is 1, m is 1, $R^1$ is hydrogen, $R^2$ is methyl, and $R^3$ is 3-chlorophenyl.

40. The compound of claim 1, wherein X is S, n is 1, m is 1, $R^1$ is hydrogen, $R^2$ is methyl, $R^3$ is 3-chlorophenyl, and $R^4$ is C(O)N(H)ipr.

* * * * *